(12) United States Patent
Kubota et al.

(10) Patent No.: US 8,507,669 B2
(45) Date of Patent: Aug. 13, 2013

(54) OPTICALLY ACTIVE DIBENZAZEPINE DERIVATIVES

(75) Inventors: Yasushi Kubota, Odawara (JP); Tsutomu Inoue, Chigasaki (JP)

(73) Assignee: Nippon Soda Co., Ltd., Tokyo (JP)

( * ) Notice: Subject to any disclaimer, the term of this patent is extended or adjusted under 35 U.S.C. 154(b) by 261 days.

(21) Appl. No.: 12/936,415

(22) PCT Filed: Apr. 8, 2009

(86) PCT No.: PCT/JP2009/001645
§ 371 (c)(1),
(2), (4) Date: Oct. 5, 2010

(87) PCT Pub. No.: WO2009/125594
PCT Pub. Date: Oct. 15, 2009

(65) Prior Publication Data
US 2011/0034688 A1    Feb. 10, 2011

(30) Foreign Application Priority Data

Apr. 11, 2008   (JP) ................. 2008-104164

(51) Int. Cl.
*C07D 491/16* (2006.01)
*C07D 317/60* (2006.01)

(52) U.S. Cl.
USPC ........................... 540/543; 540/576; 540/581

(58) Field of Classification Search
USPC ........................ 540/543, 576, 581
See application file for complete search history.

(56) References Cited

U.S. PATENT DOCUMENTS

| | | |
|---|---|---|
| 6,441,231 B1 | 8/2002 | Maruoka |
| 2008/0154036 A1 | 6/2008 | Terada et al. |

FOREIGN PATENT DOCUMENTS

| | | |
|---|---|---|
| EP | 1 712 549 A1 | 10/2006 |
| EP | 1 870 403 A1 | 12/2007 |
| JP | A-2005-225810 | 8/2005 |
| WO | WO 02/40491 A1 | 5/2002 |
| WO | WO 2005/077908 A1 | 8/2005 |
| WO | WO 2006/054366 A1 | 5/2006 |
| WO | WO 2006/104226 A1 | 10/2006 |

OTHER PUBLICATIONS

European Search Report in European Patent Application No. 09730232.7; dated May 6, 2011.

Novikov et al., "Enantioselective Olefin Epoxidation Using Novel Doubly Bridged Biphenyl Azepines as Catalysts," *Chimia*, 2007, vol. 61, pp. 236-239.

Kakei et al., Catalytic asymmetric epoxidation of α, β-unsaturated esters with chiral yttrium-biaryldiol complexes, *Chem. Asian J.*, 2007, vol. 2, pp. 257-264.

Kakei et al., "Catalytic Asymmetric Epoxidation of α, β-Unsaturated Esters Using an Yttrium-Biphenyldiol Complex," *American Chemical Society*, 2005, vol. 127, pp. 8962-8963.

Wang et al., "Design of Chiral Phase Transfer Catalyst with Conformationally Fixed Biphenyl Core: Application to Asymmetric Alkylation of Glycine Derivatives," *Organic Process Research & Development*, 2007, vol. 11, pp. 628-632.

International Search Report in International Application No. PCT/JP2009/001645; dated Jun. 2, 2009 (with English-language translation).

*Primary Examiner* — Brenda Coleman
(74) *Attorney, Agent, or Firm* — Oliff & Berridge, PLC

(57) ABSTRACT

It is to provide a novel optically active dibenzazepine derivative having a high utility value as an asymmetric phase-transfer catalyst. It is an optically active 6,7-dihydro-5H-dibenzo[c,e]azepine derivative represented by the following formula (1'), (wherein R represents a divalent organic group for cross-linking the $1^{st}$ position and the $11^{th}$ position; $R^1$ and $R^2$ are the same or different, and represent a hydrogen atom, halogen atom, or organic group, or $R^1$ and $R^2$ together represent a divalent organic group; $R^{3'}$ and $R^{4'}$ are the same or different and represent a monovalent organic group, or $R^{3'}$ and $R^{4'}$ together form an organic group that forms a cyclic structure comprising an onium nitrogen atom; Ar represents a monovalent organic group; * represents optical activity, i.e., that one axially asymmetric isomer is present in excess of the other axially asymmetric isomer with respect to a bond axis that constitutes the biphenyl structure of the compound; and $X^-$ represents a counter anion).

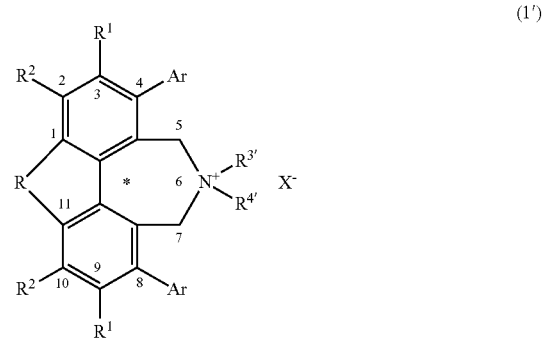

(1')

1 Claim, No Drawings

OPTICALLY ACTIVE DIBENZAZEPINE DERIVATIVES

This application is a National Stage Entry under 35 U.S.C. 371 of PCT/JP2009/001645, filed Apr. 8, 2009.

TECHNICAL FIELD

The present invention relates to an optically active dibenzazepine derivative. More specifically, the present invention relates to a novel optically active quaternary ammonium salt having a high utility value as an asymmetric phase-transfer catalyst in the fields related to the production of optically active drug substances, intermediates, starting materials, etc., mainly in the area of medical drugs and agricultural chemicals.

BACKGROUND ART

Various optically active quaternary ammonium salts having a high utility value as an asymmetric phase-transfer catalyst have been proposed. In particular, compounds having an optically active 6,7-dihydro-5H-dibenzo[c,e]azepine skeleton is useful. As examples of such compounds, there are the following compounds: a compound represented by the following formula (L-1a) described in Patent Document 1,

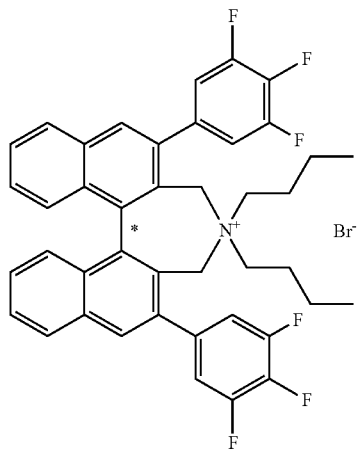

(wherein * represents optical activity, i.e., that one axially asymmetric isomer is present in excess of the other axially asymmetric isomer with respect to a bond axis that constitutes the biphenyl structure of the compound); a compound represented by the following formula (L-1b) described in Patent Document 2,

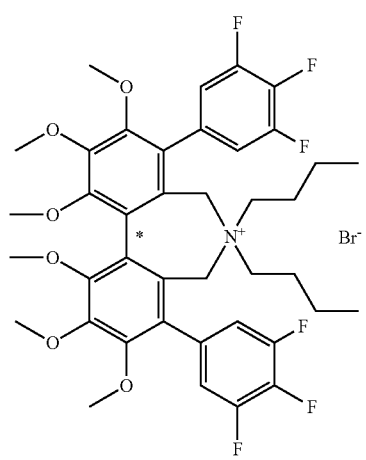

(wherein * has the same meaning as above); a compound represented by the following formula (L-1c) described in Non-Patent Document 1,

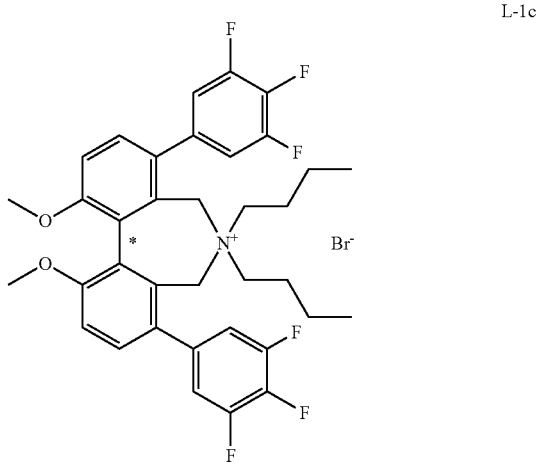 [SMILES: CCCC[N+]1(CCCC)Cc2c(-c3cc(F)c(F)c(F)c3)ccc(OC)c2-c2c(OC)ccc(-c3cc(F)c(F)c(F)c3)c2C1 ; [Br-]]

(wherein * has the same meaning as above); a compound represented by the following formula (L-1d),

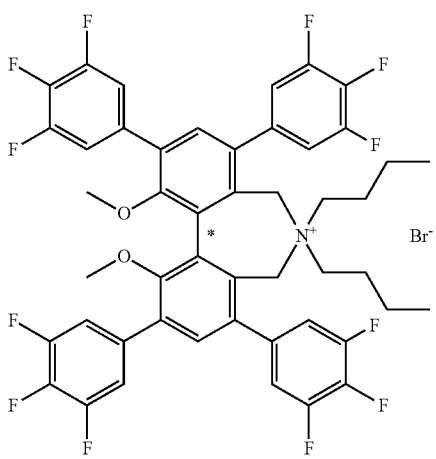

(wherein * has the same meaning as above), etc. All of these catalysts are highly useful for monoalkylation of glycine derivatives. Specifically, for example, when a compound represented by formula (L-1b) was used as a catalyst in an asymmetric monoalkylation reaction represented by the following formula (M-1),

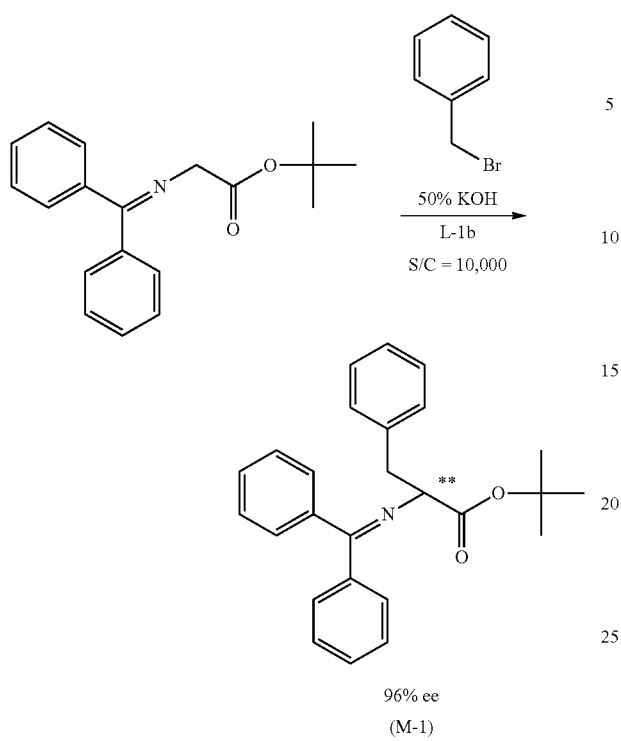

96% ee
(M-1)

(wherein  represents optical activity, i.e., that, of the two types of mirror-image isomers present on the carbon atoms shown by , one isomer is present in excess of the other isomer), the reaction was completed with a minute amount of catalyst (S/C=10,000 (S: substrate mol, C: catalyst mol) even if inexpensive potassium hydroxide was used as a base, and the optical purity of the product was 96% ee.

In contrast, when an asymmetric dialkylation reaction represented by the following formula (M-2),

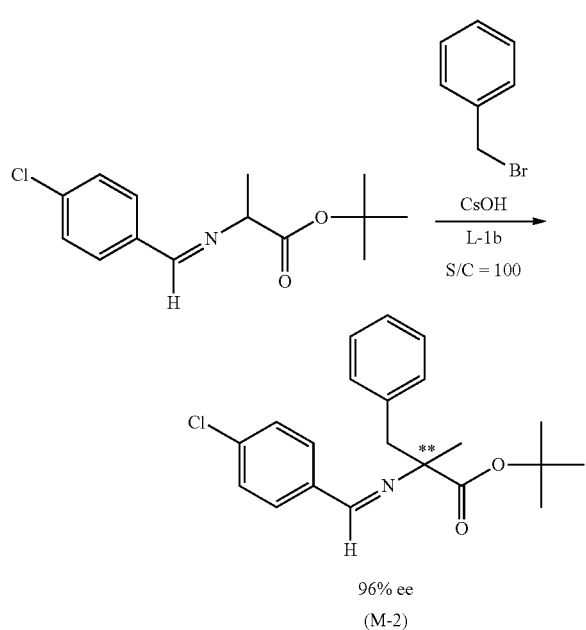

96% ee
(M-2)

(wherein ** has the same meaning as above), which is a similar reaction as the above reaction, was performed using the same catalyst and very expensive cesium hydroxide as a base, a large amount of catalyst (S/C=100) was required, although a good optical yield was obtained (Patent Document 2). In Patent Document 3, the reaction of the above formula M-2 was performed using as a catalyst a compound having the azepine skeletone represented by the following formula (L-2),

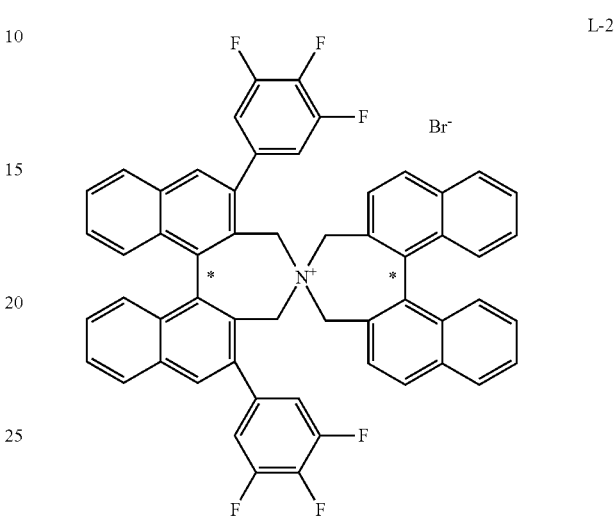

(wherein * has the same meaning as above), to obtain a similar result.

More specifically, all of the conventional optically active 6,7-dihydro-5H-dibenzo[c,e]azepine skeleton compounds had a problem, to be used as a catalyst for an asymmetric dialkylation reaction.

PRIOR ART DOCUMENTS

Patent Documents

Patent Document 1: WO2006054366
Patent Document 2: WO2006104226
Patent Document 3: U.S. Pat. No. 6,441,231

Non-Patent Documents

Non-Patent Document 1: Organic Process Research & Development 2007, 11, 628

DISCLOSURE OF THE INVENTION

Problem to be Solved by the Present Invention

The object of the present invention is to provide a novel compound having an optically active 6,7-dihydro-5H-dibenzo[c,e]azepine skeleton; and an asymmetric dialkylation reaction that confers at a high yield a product with high optical purity, by using a minute amount of the compound as a catalyst.

Means to Solve the Object

The present inventors made a keen study to solve the above problem, and have found out that a novel compound obtained by cross-linking the $1^{st}$-position and the $11^{th}$-position carbons of an optically active 6,7-dihydro-5H-dibenzo[c,e]azepine derivative exhibits a very high catalytic activity in asymmetric dialkylation reactions, and thus the present invention has been completed.

Specifically, the present invention relates to:

[1.] an optically active 6,7-dihydro-5H-dibenzo[c,e]azepine derivative represented by the following formula (1'),

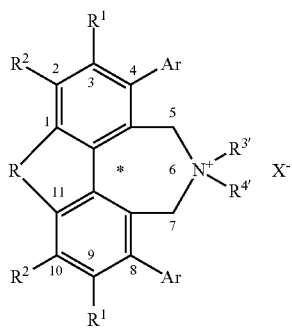

(1')

(wherein R represents a divalent organic group for crosslinking the 1$^{st}$ position and the 11$^{th}$ position;

$R^1$ and $R^2$ are the same or different, and represent a hydrogen atom, halogen atom, or organic group, or $R^1$ and $R^2$ together represent a divalent organic group;

$R^{3'}$ and $R^{4'}$ are the same or different and represent a monovalent organic group, or $R^{3'}$ and $R^{4'}$ together represent an organic group that forms a cyclic structure comprising an onium nitrogen atom;

Ar represents a monovalent organic group;

* represents optical activity, i.e., that one axially asymmetric isomer is present in excess of the other axially asymmetric isomer with respect to a bond axis that constitutes a biphenyl structure of the compound; and X⁻ represents a counter anion);

[2] the optically active 6,7-dihydro-5H-dibenzo[c,e]azepine derivative according to [1], wherein the formula (1') is represented by formula (1),

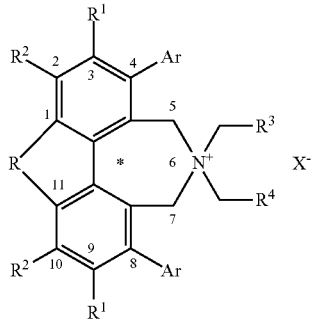

(1)

(wherein R represents a chain divalent group constituted by a carbon atom that may have a substituent, and optionally, an atom or group selected from the group consisting of a nitrogen atom that may have a substituent, oxygen atom, sulfur atom and —SO$_2$— group, in which chain divalent group a total number of those atoms or of those atoms and groups is 3 to 10;

$R^1$ and $R^2$ are the same or different, and represent a hydrogen atom, halogen atom, linear, branched, or cyclic C1-C8 alkyl group that may have a substituent, C2-C8 alkenyl group that may have a substituent, C2-C8 alkynyl group that may have a substituent, linear, branched, or cyclic C1-C8 alkoxy group that may have a substituent, C6-C14 aryl group that may have a substituent, C3-C8 heteroaryl group that may have a substituent, C1-C8 alkylcarbonyl group that may have a substituent, C1-C8 alkylsulfonyl group that may have a substituent, C6-C14 arylcarbonyl group that may have a substituent, or C6-C14 arylsulfonyl group that may have a substituent, or $R^1$ and $R^2$ together represent a divalent group which has the same definitions as R;

$R^3$ and $R^4$ are the same or different, and represent a monovalent group constituted by a carbon atom that may have a substituent, and optionally, an atom or group selected from the group consisting of a nitrogen atom that may have a substituent, oxygen atom, sulfur atom and —SO$_2$— group, in which monovalent group a total number of those atoms or of those atoms and groups is 1 to 30, or $R^3$ and $R^4$ together form a ring with —CH$_2$—N$^+$—CH$_2$—, in which ring a total number of members is 5 to 63;

Ar represents a C6-C14 aryl group that may have a substituent or C3-C8 heteroaryl group that may have a substituent; and X⁻ and * have the same meaning as above);

[3] the optically active 6,7-dihydro-5H-dibenzo[c,e]azepine derivative according to [1] or [2], wherein R in the formula (1') or formula (1) is a group represented by the following formula (2),

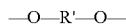

(2)

(wherein R' represents a chain divalent group consisting of a carbon atom that may have a substituent, and optionally, an oxygen atom or —SO$_2$— group, in which chain divalent group a total number of those atoms or of those atoms and groups is 1 to 8);

[4] the optically active 6,7-dihydro-5H-dibenzo[c,e]azepine derivative according to any one of [1] to [3], wherein $R^1$ and $R^2$ in the formula (1') or formula (1) are the same or different, and are a hydrogen atom, halogen atom, linear, branched, or cyclic C1-C8 alkyl group that may have a substituent, or C6-C14 aryl group that may have a substituent;

[5] the optically active 6,7-dihydro-5H-dibenzo[c,e]azepine derivative according to any one of [2] to [4], wherein $R^3$ and $R^4$ in the formula (1) are the same or different, and are a linear, branched, or cyclic C1-C30 alkyl group that may have a substituent or C6-C14 aryl group that may have a substituent, or $R^3$ and $R^4$ together are a divalent group with 2 to 60 carbons that may have a substituent; and

[6] the optically active 6,7-dihydro-5H-dibenzo[c,e]azepine derivative according to [1], wherein Ar in the formula (1') is a C6-C14 aryl group that may have a substituent or C3-C8 heteroaryl group that may have a substituent.

The present invention also relates to:

[7] an optically active biphenyl derivative represented by the following formula (3),

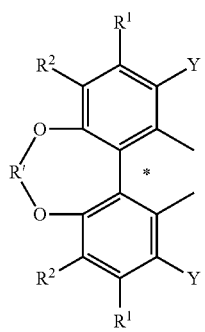

(3)

(wherein R' represents a chain divalent group consisting of a carbon atom that may have a substituent, and optionally, an oxygen atom or —SO$_2$— group, in which chain divalent group a total number of those atoms or of those atoms and groups is 1 to 8;

R$^1$ and R$^2$ are the same or different, and represent a hydrogen atom, halogen atom, linear, branched, or cyclic C1-C8 alkyl group that may have a substituent, C2-C8 alkenyl group that may have a substituent, C2-C8 alkynyl group that may have a substituent, linear, branched, or cyclic C1-C8 alkoxy group that may have a substituent, C6-C14 aryl group that may have a substituent, C3-C8 heteroaryl group that may have a substituent, C1-C8 alkylcarbonyl group that may have a substituent, C1-C8 alkylsulfonyl group that may have a substituent, C6-C14 arylcarbonyl group that may have a substituent, or C6-C14 arylsulfonyl group that may have a substituent, or R$^1$ and R$^2$ together represent a divalent organic group;

* represents optical activity, i.e., that one axially asymmetric isomer is present in excess of the other axially asymmetric isomer with respect to a bond axis that constitutes a biphenyl structure of the compound; and Y represents a sulfonate group or halogen atom).

The present invention further relates to

[8] a method for preparing an optically active α,α-disubstituted glycine derivative represented by the following formula (B),

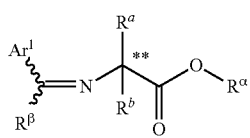

(B)

(wherein R$^\alpha$ represents a linear, branched, or cyclic C1-C8 alkyl group that may have a substituent, C6-C14 aryl group that may have a substituent, C3-C8 heteroaryl group that may have a substituent, or C7-C16 aralkyl group that may have a substituent;

R$^\beta$ represents a hydrogen atom, linear, branched, or cyclic C1-C8 alkyl group, C6-C14 aryl group that may have a substituent, or C7-C16 aralkyl group that may have a substituent;

R$^a$ represents an organic group;

R$^b$ represents an organic group that is different from R$^a$;

Ar' represents a C6-C14 aryl group that may have a substituent;

bond axes shown by wavy lines represent that a configuration of a substituent on a carbon atom replaced by these bond axes is not limited; and represents optical activity, i.e., that of two types of mirror-image isomers present on the carbon atoms shown by , one isomer is present in excess of the other isomer), the method comprising reacting an α-substituted glycine derivative represented by the following formula (A),

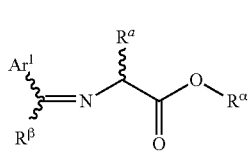

(A)

(wherein R$^\alpha$, R$^\beta$, R$^a$, Ar' and bond axes shown by the wavy lines have the same meaning as above) with a compound of the following formula (C), R$^b$Z (C)

(wherein R$^b$ has the same meaning as above and Z represents a leaving group) in the presence of the optically active 6,7-dihydro-5H-dibenzo[c,e]azepine derivative according to any one of (1] to [6]; and

[9] a method for preparing an optically active α-monosubstituted glycine derivative represented by the following formula (B'),

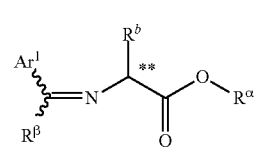

(B')

(wherein R$^\alpha$ represents a linear, branched, or cyclic C1-C8 alkyl group that may have a substituent, C6-C14 aryl group that may have a substituent, C3-C8 heteroaryl group that may have a substituent, or C7-C16 aralkyl group that may have a substituent;

R$^\beta$ represents a hydrogen atom, linear, branched, or cyclic C1-C8 alkyl group, C6-C14 aryl group that may have a substituent, or C7-C16 aralkyl group that may have a substituent;

R$^b$ represents an organic group;

Ar' represents a C6-C14 aryl group that may have a substituent;

bond axes shown by wavy lines represent that a configuration of a substituent on a carbon atom replaced by these bond axes is not limited; and

** represents optical activity, i.e., that, of two types of mirror-image isomers present on the carbon atoms shown by one isomer is present in excess of the other isomer), the method comprising reacting a glycine derivative represented by the following formula (A'),

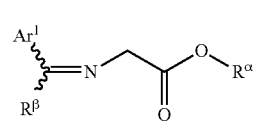

(A')

(wherein R$^\alpha$, R$^\beta$, Ar' and bond axes shown by the wavy lines have the same meaning as above) with a compound of the following formula (C), R$^b$Z (C)

(wherein R$^b$ has the same meaning as above and Z represents a leaving group) in the presence of the optically active 6,7-dihydro-5H-dibenzo[c,e]azepine derivative according to any one of [1] to [6].

DESCRIPTIONS OF EMBODIMENTS

Hereinbelow, the present invention will be explained in detail.

1-1. Optically Active 6,7-dihydro-5H-dibenzo[c,e]azepine derivative

Substituents of the optically active 6,7-dihydro-5H-dibenzo[c,e]azepine derivative represented by the following formula (1'),

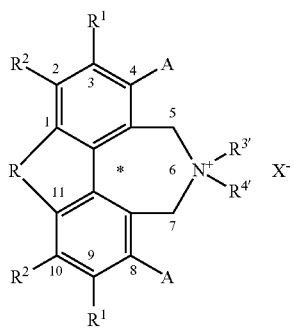

(1')

re as described in the following.

(R)

R represents a divalent organic group for cross-linking the $1^{st}$ position and the $11^{th}$ position. More specifically, R represents a chain divalent group constituted by a carbon atom that may have a substituent, and optionally, an atom or group selected from the group consisting of a nitrogen atom that may have a substituent, oxygen atom, sulfur atom and —$SO_2$— group, in which chain divalent group the total number of those atoms or of those atoms and groups is 3 to 10, etc.

In this context, the term "optionally" means that R has carbon atoms that may have a substituent, and if chemically possible, part of those carbon atoms can be appropriately replaced by an atom or group selected from the group consisting of a nitrogen atom that may have a substituent, oxygen atom, sulfur atom and —$SO_2$— group. This term also has the same meaning in $R^{3'}$ (or $R^3$) and $R^{4'}$ (or $R^4$) described hereinafter.

A "carbon atom that may have a substituent" means a —$CH_2$— group that may have a substituent, and examples of such substituent encompass a halogen atom, linear, branched, or cyclic C1-C8 alkyl group, linear, branched, or cyclic C1-C8 alkoxy group, oxo group, aryl group that may have a substituent, arylcarbonyl group that may have a substituent, alkylcarbonyl group that may have a substituent, arylsulfonyl group that may have a substituent, and alkylsulfonyl group that may have a substituent.

In this context, a "halogen atom" encompasses fluorine, chlorine, bromine, and iodine. A "linear, branched, or cyclic C1-C8 alkyl group" encompasses methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, cyclopropylmethyl, cyclopentyl, etc.

A "linear, branched, or cyclic C1-C8 alkoxy group" encompasses methoxy, ethoxy, propoxy, isopropoxy, butoxy, isobutoxy, sec-butoxy, tert-butoxy, pentyloxy, isopentyloxy, hexyloxy, heptyloxy, octyloxy, cyclopropoxy, cyclobutoxy, 2-methylcyclopropoxy, cyclopropylmethoxy, cyclopentyloxy group, etc.

An "aryl group that may have a substituent" means a monocyclic or polycyclic aryl group. In this context, in the case of a polycyclic aryl group, a partly saturated group is encompassed in addition to a fully unsaturated group. Examples of the aryl group encompass phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 10-phenanthrylphenyl, azulenyl, indenyl, indanyl, tetralinyl, etc., and a C6-C10 aryl group is preferred.

The "aryl group" of an "arylcarbonyl group that may have a substituent" and "arylsulfonyl group that may have a substituent" encompasses the same as those described in the above "aryl group".

The "alkyl group" of an "alkylcarbonyl group that may have a substituent" and "alkylsulfonyl group that may have a substituent" encompasses the same as those described in the above C1-C8 alkyl group.

A "nitrogen atom that may have a substituent" means an —NH— group that may have a substituent, and examples of the substituent encompass a linear, branched, or cyclic C1-C8 alkyl group, aryl group that may have a substituent, arylcarbonyl group that may have a substituent, alkylcarbonyl group that may have a substituent, arylsulfonyl group that may have a substituent, and alkylsulfonyl group that may have a substituent.

In this context, the alkyl group, aryl group, arylcarbonyl group, alkylcarbonyl group, arylsulfonyl group, and alkylsulfonyl group are respectively the same as those defined in the above carbon atom that may have a substituent.

Examples of the "substituent" in the above "aryl group that may have a substituent", "arylcarbonyl group that may have a substituent", "alkylcarbonyl group that may have a substituent", "arylsulfonyl group that may have a substituent", and "alkylsulfonyl group that may have a substituent" include the followings:

a halogen atom such as fluorine, chlorine, bromine, and iodine;

a linear, branched, or cyclic C1-C8 alkyl group such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl, among which more preferred examples of the alkyl group include a linear, branched, or cyclic C1-C8 alkyl group wherein at the α position, there is a secondary or tertiary carbon, such as isopropyl, sec-butyl, tert-butyl, tert-pentyl, tert-hexyl, tert-heptyl, tert-octyl, cyclopropyl, cyclobutyl, and cyclopentyl;

a C6-C14 aryl group such as phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, and 1D-phenanthryl; and a linear, branched, or cyclic C1-C8 alkoxy group such as methoxy, ethoxy, propoxy, isopropoxy, butoxy, isobutoxy, sec-butoxy, tent-butoxy, pentyloxy, isopentyloxy, hexyloxy, heptyloxy, octyloxy, cyclopropoxy, cyclobutoxy, 2-methylcyclopropoxy, cyclopropylmethoxy, and cyclopentyloxy.

In the case where a nitrogen atom is included in the atoms that constitute a divalent chain organic group cross-linking the $1^{st}$ position and the $11^{th}$ position of a compound (1'), (1) when the nitrogen atom has been substituted by any of the above alkylcarbonyl group, arylcarbonyl group, alkylsulfonyl group, and arylsulfonyl group, a carbon atom adjacent to the nitrogen atom may or may not be substituted by an oxo group; and (2) when the nitrogen atom has been substituted by a group other than the above alkylcarbonyl group, arylcarbonyl group, alkylsulfonyl group, and arylsulfonyl group, the carbon atom adjacent to the nitrogen atom is substituted by an oxo group.

Preferred examples of "R" include the following groups:
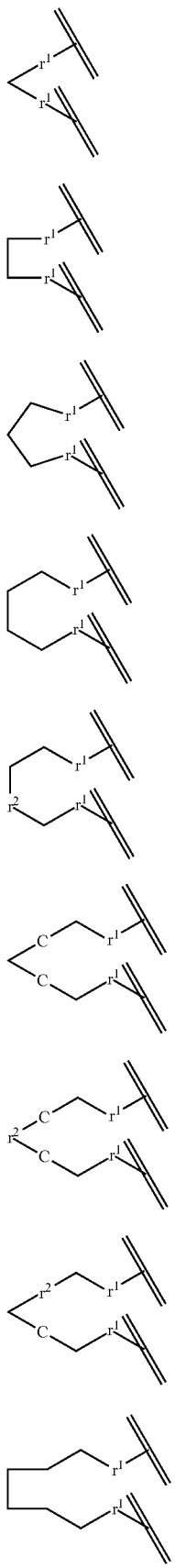
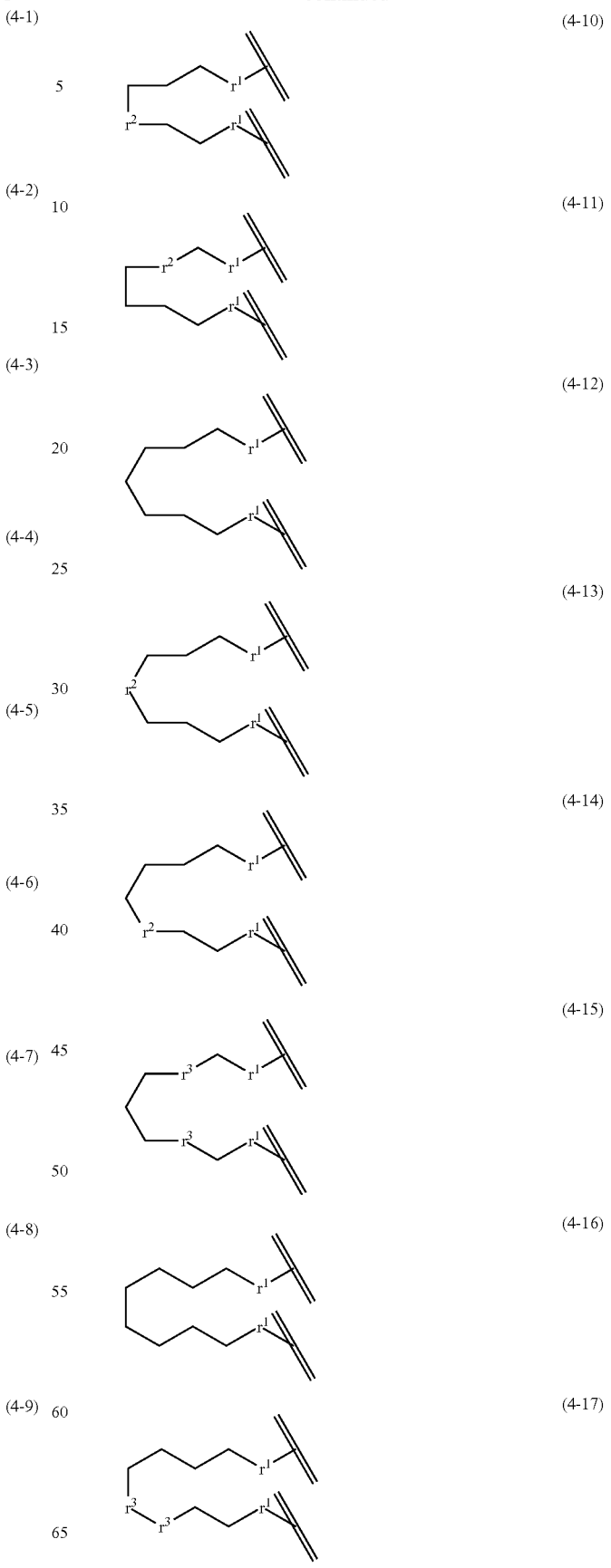

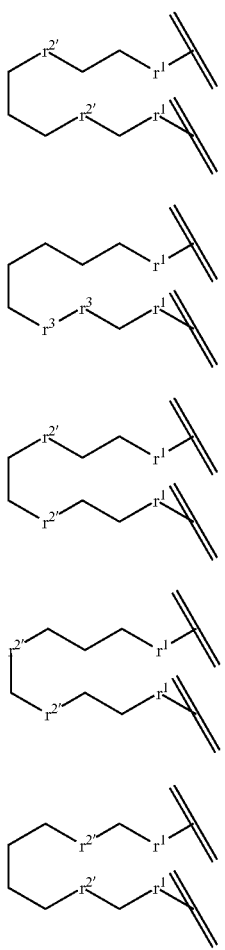

(4-18)

(4-19)

(4-20)

(4-21)

(4-22)

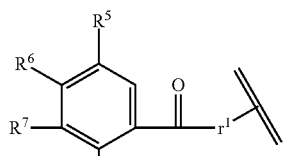

(5-1)

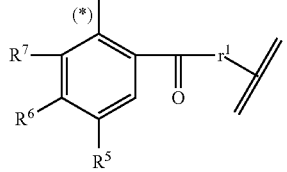

(5-2)

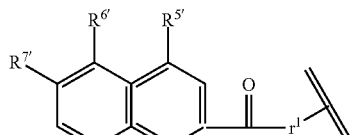

(5-3)

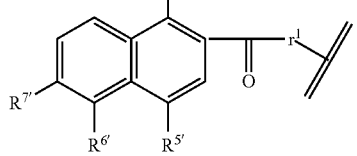

(5-4)

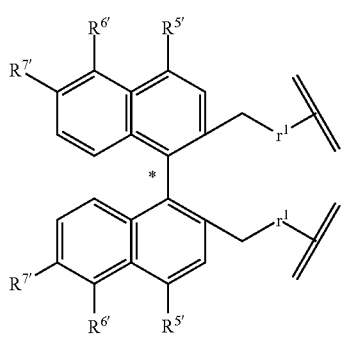

[wherein two $r^1$s that are components of the divalent organic group are hetero atoms that are the same or different from each other (hereinafter, the term "hetero atom" means any of each atom of a nitrogen atom that may have a substituent, oxygen atom, and sulfur atom, or —SO$_2$— group), or show that one of them is a hetero atom and the other is a carbon atom; one $r^2$ that is a component of the divalent organic group shows that it is a hetero atom; two $r^3$s that are component of the divalent organic group show that one of them is a hetero atom and the other is a carbon atom; and two $r^2$'s that are components of the divalent organic group are, independently of $r^1$, hetero atoms that are the same or different from each other, or show that one of them is a hetero atom and the other is a carbon atom.

Among these, the groups (4-1), (4-2), (4-3), (4-4), (4-6), (4-7), (4-9), (4-12), (4-13) (4-16), and (4-20), are particularly preferred.

Further, examples of Rs include the groups of the following formulae (5-1), (5-2), (5-3), and (5-4) that may have a substituent,

[wherein $R^5$, $R^6$, $R^7$, $R^{5'}$, $R^{6'}$, and $R^{7'}$ are the same or different, and represent a hydrogen atom, halogen atom, linear, branched, or cyclic C1-C8 alkyl group that may have a substituent, C2-C8 alkenyl group that may have a substituent, C2-C8 alkynyl group that may have a substituent, C6-C14 aryl group that may have a substituent, C3-C8 heteroaryl group that may have a substituent, or linear, branched, or cyclic C1-C8 alkoxy group that may have a substituent; or $R^5$ and $R^6$, $R^6$ and $R^7$, or two $R^7$s, or $R^{6'}$ and $R^{7'}$ together represent that they are a divalent group selected appropriately from the groups as defined in the above R;

$r^1$ has the same meaning as above; * represents optical activity, i.e., that one axially asymmetric isomer is present in excess of the other axially asymmetric isomer with respect to a bond axis that constitutes a biphenyl structure of the substituent; and (*) has the same meaning as the above *, although it represents non-optical activity when R⁷ is a hydrogen. Among these, groups (5-1) and (5-2) are particularly preferred.

In the above formula (1') or (1), R is preferably a group represented by formula (2),

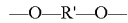  (2)

[wherein R' represents a chain divalent group consisting of a carbon atom that may have a substituent, and optionally, an oxygen atom or —SO₂— group, in which chain divalent group the total number of those atoms or of those atoms and groups is 1 to 11, where the "carbon atom that may have a substituent" is same as those defined above].

For example, in formulae (4-1) to (4-22) and formulae (5-1) to (5-4), the case wherein r¹ is an oxygen atom is preferred.

($R^1$, $R^2$)

$R^1$ and $R^2$ are the same or different, and are a hydrogen atom, halogen atom, or organic group, or $R^1$ and $R^2$ together represent a divalent organic group which is same as the above R.

The organic group encompasses a linear, branched, or cyclic C1-C8 alkyl group that may have a substituent, C2-C8 alkenyl group that may have a substituent, C2-C8 alkynyl group that may have a substituent, linear, branched, or cyclic C1-C8 alkoxy group that may have a substituent, C6-C14 aryl group that may have a substituent, C3-C8 heteroaryl group that may have a substituent, C1-C8 alkylcarbonyl group that may have a substituent, C1-C8 alkylsulfonyl group that may have a substituent, C6-C14 arylcarbonyl group that may have a substituent, and C6-C14 arylsulfonyl group that may have a substituent.

In this context, a "halogen atom" encompasses fluorine, chlorine, bromine, and iodine. The "linear, branched, or cyclic C1-C8 alkyl group" of a "linear, branched, or cyclic C1-C8 alkyl group that may have a substituent" encompasses a linear, branched, or cyclic C1-C8 alkyl group such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl, and more preferably, a linear, branched, or cyclic C1-C8 alkyl group wherein at the α position, there is a secondary or tertiary carbon, such as isopropyl, sec-butyl, tert-butyl, tert-pentyl, tert-hexyl, tert-heptyl, tert-octyl, cyclopropyl, cyclobutyl, and cyclopentyl.

The "C2-C8 alkenyl group" of a "C2-C8 alkenyl group that may have a substituent" encompasses vinyl, 1-propenyl allyl, 1-butenyl, 2-butenyl, 3-butenyl 1-methyl-2-propenyl, 2-methyl-2-propenyl, 1-pentenyl, 2-pentenyl, 3-pentenyl, 4-pentenyl, 1-methyl-2-butenyl, 2-methyl-2-butenyl, 1-hexenyl, 2-hexenyl, 3-hexenyl, 4-hexenyl, 5-hexenyl, 1-heptenyl, 6-heptenyl, 1-octenyl, 7-octenyl, etc.

The "C2-C8 alkynyl group" of a "C2-C8 alkynyl group that may have a substituent" encompasses ethynyl, 1-propynyl, propargyl, 1-butynyl, 2-butynyl, 3-butynyl, 1-methyl-2-propynyl, 2-methyl-3-butynyl, 1-pentynyl, 2-pentynyl, 3-pentynyl, 4-pentynyl, 1-methyl-2-butynyl, 2-methyl-3-pentynyl, 1-hexynyl, 1,1-dimethyl-2-butynyl, etc.

The "linear, branched, or cyclic C1-C8 alkoxy group" of a "linear, branched, or cyclic C1-C8 alkoxy group that may have a substituent" encompasses methoxy, ethoxy, propoxy, isopropoxy, butoxy, isobutoxy, sec-butoxy, tert-butoxy pentyloxy, isopentyloxy, hexyloxy, heptyloxy, octyloxy, cyclopropoxy, cyclobutoxy, 2-methylcyclopropoxy cyclopropylmethoxy, cyclopentyloxy, etc.

The "C6-C14 aryl group" of a "C6-C14 aryl group that may have a substituent" encompasses phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 10-phenanthryl, azulenyl, indenyl, indanyl, tetralinyl, etc.

The "C3-C8 heteroaryl group" of a "C3-C8 heteroaryl group that may have a substituent" means a monocyclic or polycyclic C3-C8 aryl group having 1 to 3 nitrogen atom, oxygen atom, or sulfur atom, and for example, encompasses 2-pyridyl, 3-pyridyl, 4-pyridyl, 2-quinolyl, 3-quinolyl, 4-quinolyl, 5-quinolyl, 6-quinolyl, 7-quinolyl, 8-quinolyl, 2-indolyl, 3-indolyl, 4-indolyl, 5-indolyl, 6-indolyl, 7-indolyl, 2-furyl, 3-furyl, 2-thienyl, 3-thienyl, 2-pyrrolidyl, 3-pyrrolidyl, 2-imidazolyl, 4-imidazolyl, 5-imidazolyl, 2-oxazolyl, 4-oxazolyl, 5-oxazolyl, 2-thiazolyl, 4-thiazolyl, 5-thiazolyl, etc.

The "alkyl group" of a "C1-C8 alkylcarbonyl group that may have a substituent" and "C1-C8 alkylsulfonyl group that may have a substituent" is same as those defined in the above "linear, branched, or cyclic C1-C8 alkyl group".

The "C6-C14 aryl group" of a "C6-C14 arylcarbonyl group that may have a substituent" and "C6-C14 arylsulfonyl group that may have a substituent" is same as those defined in the above "C6-C14 aryl group".

Examples of the "substituent" in the above phrase "that may have a substituent" encompass the followings:

a halogen atom such as fluorine, chlorine, bromine and iodine;

a linear, branched, or cyclic C1-C8 alkyl group such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl, among which more preferred examples of the alkyl group include a linear, branched, or cyclic C1-C8 alkyl group wherein at the α position, there is a secondary or tertiary carbon, such as isopropyl, sec-butyl, tert-butyl, tart-pentyl, tert-hexyl, tert-heptyl, tert-octyl, cyclopropyl, cyclobutyl, and cyclopentyl;

a C6-C14 aryl group such as phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, and 10-phenanthryl; and a linear, branched, or cyclic C1-C8 alkoxy group such as methoxy, ethoxy, propoxy, isopropoxy, butoxy, isobutoxy, sec-butoxy, tent-butoxy, pentyloxy, isopentyloxy, hexyloxy, heptyloxy, octyloxy, cyclopropoxy, cyclobutoxy, 2-methylcyclopropoxy, cyclopropylmethoxy, and cyclopentyloxy.

($R^3$, $R^{3'}$, $R^4$, $R^{4'}$)

$R^{3'}$ and $R^{4'}$ are substituents with which the nitrogen atom in the optically active 6,7-dihydro-5H-dibenzo[c,e]azepine skeleton represented by formula (1') form an onium. $R^{3'}$ and $R^{4'}$ are the same or different monovalent organic group, or an organic group wherein the nitrogen atom in the azepine skeleton and the $R^{3'}$ and $R^{4'}$ together form a cyclic structure.

Specifically, the monovalent organic group shows those constituted by a carbon atom that may have a substituent, and optionally, an atom or group selected from the group consisting of a nitrogen atom that may have a substituent, oxygen atom, sulfur atom and —SO₂— group, in which the total number of those atoms or of those atoms and groups is 1 to 31.

The organic group wherein the nitrogen atom in the azepine skeleton and $R^{3'}$ and $R^{4'}$ together form a cyclic structure (hereinafter, sometimes referred to as an "organic group forming a cyclic structure") is constituted by, in addition to the nitrogen atom of the azepine skeleton, a carbon atom that may have a substituent, and optionally, an atom or group selected from the group consisting of a nitrogen atom that may have a substituent, oxygen atom, sulfur atom and —SO$_2$— group, and the total number of the nitrogen atom in the azepine skeleton and those atoms or those atoms and groups is 5 to 63.

In this context, a "carbon atom that may have a substituent" and a "nitrogen atom that may have a substituent" have the same definitions as the "carbon atom that may have a substituent" and the "nitrogen atom that may have a substituent" in the above R.

These monovalent organic group or organic group forming a cyclic structure is preferably bound to the nitrogen atom in the azepine skeleton via an unsubstituted carbon atom, as shown by the compound represented by formula (1). Specifically, a preferred $R^{3'}$ is —CH$_2$—$R^3$ and similarly, a preferred $R^{4'}$ is —CH$_2$—$R^4$.

$R^3$ and $R^4$ are the same or different, and show those constituted by a carbon atom that may have a substituent, and optionally, an atom or group selected from the group consisting of a nitrogen atom that may have a substituent, oxygen atom, sulfur atom and —SO$_2$— group, in which the total number of those atoms or of those atoms and groups is 1 to 30.

The organic group wherein the nitrogen atom in the azepine skeleton, two methylenes, and $R^3$ and $R^4$ together form a cyclic structure (hereinafter, sometimes referred to as an "organic group forming a cyclic structure") is constituted by, in addition to the nitrogen atom in the azepine skeleton, a carbon atom that may have a substituent, and optionally, an atom or group selected from the group consisting of a nitrogen atom that may have a substituent, oxygen atom, sulfur atom and —SO$_2$— group. The total number of the nitrogen atom in the azepine skeleton, two methylenes, and those atoms or those atoms and groups is 5 to 63.

In this context, a "carbon atom that may have a substituent" and a "nitrogen atom that may have a substituent" have the same definitions as the "carbon atom that may have a substituent" and the "nitrogen atom that may have a substituent" in the above R.

Examples of the "substituent" of a "carbon atom that may have a substituent" encompass a halogen atom, oxo group, linear, branched, or cyclic C1-C8 alkyl group, linear, branched, or cyclic C1-C8 alkoxy group, C6-C14 aryl group that may have a substituent, and C7-C16 aralkyl group that may have a substituent.

In this context, a "halogen atom" encompasses fluorine, chlorine, bromine, iodine, etc.

A "linear, branched, or cyclic C1-C8 alkyl group" encompasses methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, cyclopentyl, etc.

A "linear, branched, or cyclic C1-C8 alkoxy group" encompasses methoxy, ethoxy, propoxy, isopropoxy, butoxy, isobutoxy, sec-butoxy, tert-butoxy, pentyloxy, isopentyloxy, hexyloxy, heptyloxy, octyloxy, cyclopropoxy, cyclobutoxy, 2-methylcyclopropoxy, cyclopropylmethoxy, cyclopentyloxy, etc.

The "C6-C14 aryl group" of a "C6-C14 aryl group that may have a substituent" encompasses phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 10-phenanthryl, azulenyl, indenyl, indenyl, tetralinyl, etc.

The "C7-C16 aralkyl group" of a "C7-C16 aralkyl group that may have a substituent" encompasses a C7-C16 aralkyl group such as benzyl, 2-phenylethyl, 1-naphthylmethyl, 2-naphthylmethyl, etc.

0 to 2 of these substituents can be used to substitute the same carbon atom and when there are two substituents, substituents that are different from each other can be used for the substitution.

Examples of the "substituent" of a "nitrogen atom that may have a substituent" encompass a linear, branched, or cyclic C1-C8 alkyl group, linear, branched, or cyclic C1-C8 alkylcarbonyl group, linear, branched, or cyclic C1-C8 alkylsulfonyl group, C6-C14 aryl group that may have a substituent, C6-C14 arylcarbonyl group that may have a substituent, C6-C14 arylsulfonyl group that may have a substituent, C7-C16 aralkyl group that may have a substituent, C7-C16 aralkylcarbonyl group that may have a substituent, and C7-C16 aralkylsulfonyl group that may have a substituent.

In this context, a "linear, branched, or cyclic C1-C8 alkyl group", "C6-C14 aryl group that may have a substituent" and "C7-C16 aralkyl group that may have a substituent" are the same as those defined in the above "carbon atom that may have a substituent".

A "linear, branched, or cyclic C1-C8 alkylcarbonyl group" is a group wherein a linear, branched, or cyclic C1-C8 alkyl group and carbonyl group are bound, and a "linear, branched, or cyclic C1-C8 alkyl group" encompasses methyl, ethyl, propyl, isopropyl, butyl, isobutyl, sec-butyl, tent-butyl, pentyl, isopentyl, neopentyl, hexyl, isohexyl, heptyl, isoheptyl, octyl, isooctyl, decyl, dodecyl, cyclopropyl, cyclobutyl, 2-methylcyclopropyl, cyclopropylmethyl, and cyclopentyl.

A "linear, branched, or cyclic C1-C8 alkylsulfonyl group" is a group wherein C1-C8 alkyl group and a sulfonyl group are bound, and the "C1-C8 alkyl group" is same as those defined in the above "C1-C8 alkylcarbonyl group".

The "C6-C14 arylsulfonyl group" of a "C6-C14 arylsulfonyl group that may have a substituent" is a group wherein a C6-C14 aryl group and a sulfonyl group are bound, and the "C6-C14 aryl group" is same as those defined in the above "carbon atom that may have a substituent".

The "C6-C14 arylcarbonyl group" of a "C6-C14 arylcarbonyl group that may have a substituent" is a group wherein a C6-C14 aryl group and a carbonyl group are bound, and the "C6-C14 aryl group" is same as those defined in the above "carbon atom that may have a substituent".

The "C7-C16 aralkylcarbonyl group" of a "C7-C16 aralkylcarbonyl group that may have a substituent" is a group wherein a C7-C16 aralkyl group and a carbonyl group are bound, and the "C7-C16 aralkyl group" is same as those defined in the above "carbon atom that may have a substituent".

The "C7-C16 aralkylsulfonyl group" of a "C7-C16 aralkylsulfonyl group that may have a substituent" is a group wherein a C7-C16 aralkyl group and a sulfonyl group are bound, and the "C7-C16 aralkyl group" is same as those defined in the above "carbon atom that may have a substituent".

Examples of the "substituent" in the above "C6-C14 aryl group that may have a substituent", "C7-C16 aralkyl group that may have a substituent", etc. encompass:

a halogen atom such as fluorine, chlorine, bromine and iodine;

a linear, branched, or cyclic C1-C8 alkyl group such as methyl, ethyl, propyl, isopropyl, butyl, isobutyl, sec-butyl, tent-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl;

a linear, branched, or cyclic C1-C8 alkoxy group such as methoxy, ethoxy, propoxy, isopropoxy, butoxy, isobutoxy, sec-butoxy, tert-butoxy, pentyloxy, isopentyloxy, hexyloxy, heptyloxy, octyloxy, cyclopropoxy, cyclobutoxy, 2-methylcyclopropoxy, cyclopropylmethoxy, and cyclopentyloxy.

In a case where a nitrogen atom is included in atoms constituting the above monovalent organic group or the above organic group forming a cyclic structure, (1) when the nitrogen atom has been substituted by any of the above alkylcarbonyl group, arylcarbonyl group, aralkylcarbonyl group, alkylsulfonyl group, arylsulfonyl group, and aralkylsulfonyl group, the carbon atom adjacent to the nitrogen atom may or may not be substituted by an oxo group; and (2) when the nitrogen atom has been substituted by a group other than the above alkylcarbonyl group, arylcarbonyl group, aralkylcarbonyl group, alkylsulfonyl group, arylsulfonyl group, and aralkylsulfonyl group, the carbon atom adjacent to the nitrogen atom is substituted by an oxo group.

In formula (1), a preferred $R^3$ and $R^4$ are the same or different linear, branched, or cyclic C1-C30 alkyl group that may have a substituent, more preferably a linear or branched C1-C8 alkyl group, or a C6-C14 aryl group that may have a substituent, or $R^3$ and $R^4$ together form a divalent group with 2 to 60 carbons that may have a substituent. Examples of the above divalent group with 2 to 60 carbons that may have a substituent encompass those listed in the following as formulae (6-1) to (6-20).

However, formulae (6-1) to (6-20) also include and show the carbon atom adjacent to $R^3$ and $R^4$, i.e., represent the specific examples of the following formula (6):

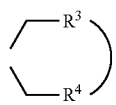

(6)

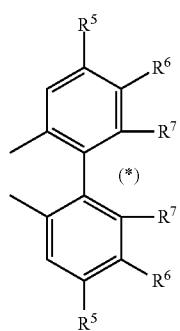

(6-1)

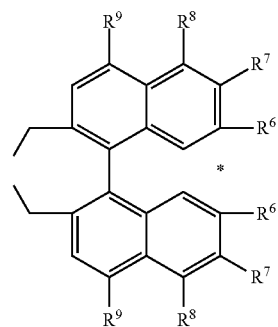

(6-2)

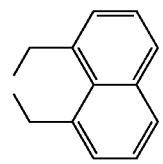

(6-3)

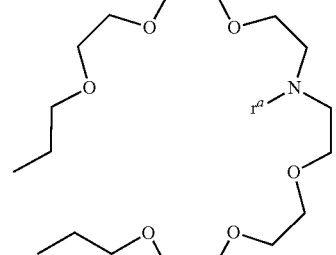

(6-4)

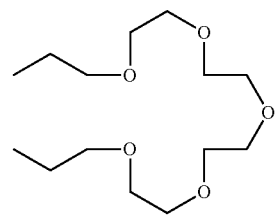

(6-5)

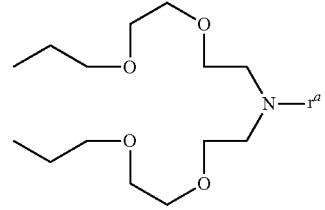

(6-6)

(6-10)

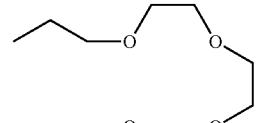

(6-7)

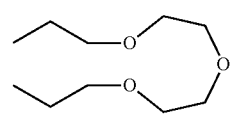

(6-8)

-continued (6-9) 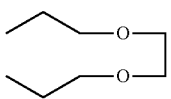

(6-11) 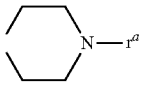

(6-12) 

(6-11) 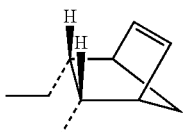

(6-12) 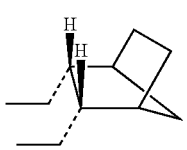

(6-13) 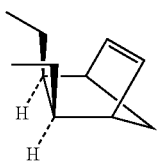

(6-14) 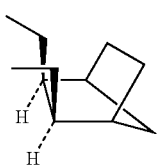

(6-15) 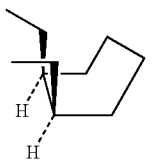

(6-16) 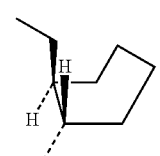

(6-17) 

(6-18) 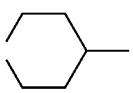

(6-19) 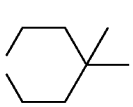

-continued (6-20) 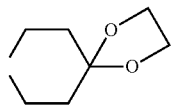

(wherein $R^5$ and $R^6$, and $R^6$ and $R^7$ are substituents defined in $R^1$ and $R^2$, respectively; $R^8$ and $R^9$ each independently represent a hydrogen atom or halogen atom; and $r^a$ represents a linear, branched, or cyclic C1-C8 alkylcarbonyl group, linear, branched, or cyclic C1-C8 alkylsulfonyl group, C6-C14 aryl group that may have a substituent, C6-C14 arylcarbonyl group that may have a substituent, C6-C14 arylsulfonyl group that may have a substituent, C7-C16 aralkylcarbonyl group that may have a substituent, or C7-C16 aralkylsulfonyl group that may have a substituent).

The definitions of respective groups in $R^8$, $R^9$ and $r^a$ are same as the definitions of those groups in the above "carbon atom that may have a substituent" and "nitrogen atom that may have a substituent".

(Ar)

Ar represents a monovalent organic group, and preferably a C6-C14 aryl group that may have a substituent or a C3-C8 heteroaryl group that may have a substituent.

Ar is more preferably a C6-C14 aryl group that may have a substituent or a C3-C8 heteroaryl group that may have a substituent, and particularly preferably a C6-C14 aryl group.

In this context, the definitions of "C6-C14 aryl group" and "C3-C8 heteroaryl group", respectively, are same as the definitions of those groups in $R^1$ and $R^2$.

Examples of the "substituent" in the phrase "that may have a substituent" encompass a halogen atom, linear, branched, or cyclic C1-C8 alkyl group, linear, branched, or cyclic C1-C8 alkoxy group, linear, branched, or cyclic C1-C8 alkylcarbonyl group, linear, branched, or cyclic C1-C8 alkylsulfonyl group, C6-C14 arylcarbonyl group that may have a substituent, and C6-C14 arylsulfonyl group that may have a substituent.

In this context, the definitions of the respective groups are same as those defined in the above $R^3$, $R^{3'}$, $R^4$ and $R^{4'}$.

(Others)

* represents optical activity, i.e., that one axially asymmetric isomer is more excessive than the other axially asymmetric isomer with respect to a bond axis that constitutes the biphenyl-skeleton structure of the compound of (1') or (1) of the present application.

$X^-$ is not particularly limited as long as it is a counter anion of ammonium, and encompasses anions such as:

a hydroxide ion, a halogen atom ion such as fluorine, chlorine, bromine, and iodine, a sulfonic-acid ion such as $HSO_3—$ and $r^bSO_4—$, a phosphoric-acid ion such as $H_2PO_4—$ and $PO_3—$, and a carboxylic-acid ion such as $r^bCO_2—$.

In this context, $r^b$ encompasses a hydrogen atom, linear, branched, or cyclic C1-C8 alkyl group and C6-C14 aryl group that may have a substituent.

A "linear, branched, or cyclic C1-C8 alkyl group" encompasses methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, cyclopentyl, etc.

The "C6-C14 aryl group" of a "C6-C14 aryl group that may have a substituent" encompasses phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 10-phenanthryl, azulenyl, indenyl, indanyl, tetralinyl, etc.

Examples of the "substituent" in the phrase "that may have a substituent" encompass a halogen atom, linear, branched, or cyclic C1-C8 alkyl group, and linear, branched, or cyclic C1-C8 alkoxy group.

In this context, the definitions of respective group of the "linear, branched, or cyclic C1-C8 alkyl group" and "linear, branched, or cyclic C1-C8 alkoxy group" are same as the definitions of those groups in the above $R^1$ and $R^2$, or $R^{3'}$ (or $R^3$) and $R^{4'}$ (or $R^4$).

1-2. Method for Preparing Optically Active 6,7-dihydro-5H-dibenzo[c,e]azepine derivative Among optically active 6,7-dihydro-5H-dibenzo[c,e] azepine derivatives of the present invention, for example, a compound represented by formula (1a) can be prepared by the method represented by the following reaction formula (D),

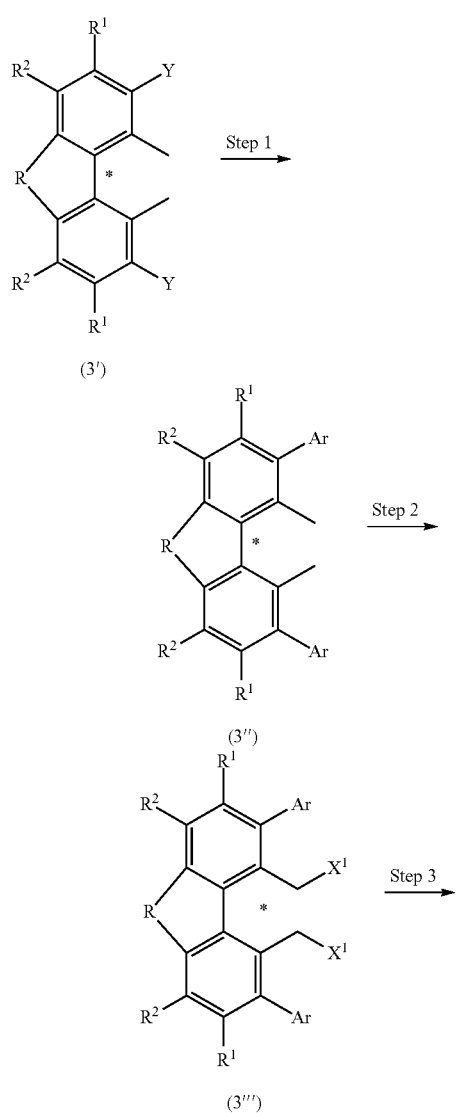

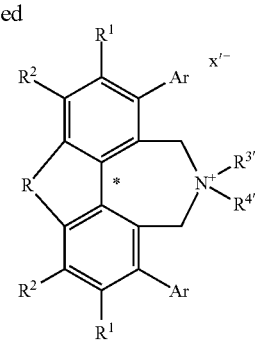

[wherein R, $R^1$, $R^2$, $R^{3'}$, $R^{4'}$, Ar, and * have the same meaning as above, and $x^1$ represents a halogen atom such as chlorine, bromine, and iodine].

Specifically, the compound is prepared through respective steps of:

step 1 of alylating an optically active biphenyl derivative represented by compound (3') which is a starting material, to obtain an optically active diarylbiphenyl derivative represented by compound (3"),

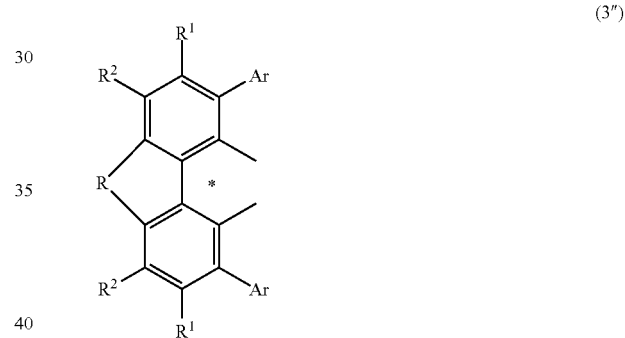

[wherein R, $R^1$, $R^2$, Ar, and * have the same meaning as above];

step 2 of halogenating compound (3") to obtain an optically active bis-benzyl halide represented by compound (3''')

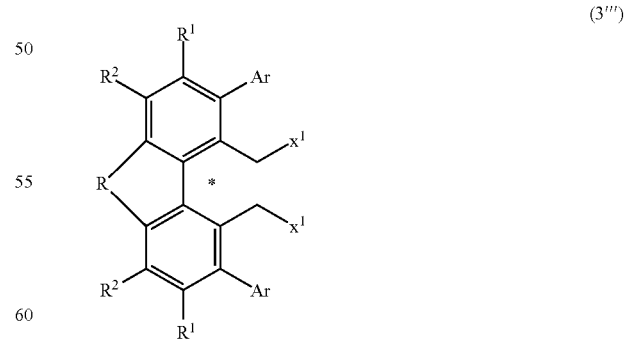

[wherein R, $R^1$, $R^2$, Ar, *, and $x^1$ have the same meaning as above]; and step 3 of aminating compound (3''') to obtain an optically active 6,7-dihydro-5H-dibenzo[c,e]azepine derivative represented by formula (1a),

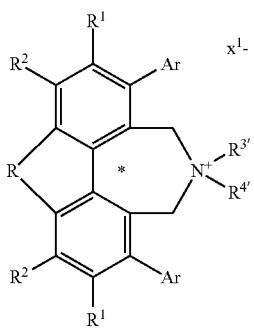

(1a)

[wherein R, $R^1$, $R^2$, $R^{3'}$, $R^{4'}$, Ar, *, and $x^1$ have the same meaning as above].

Each step is explained below.

Step 1 comprises allowing a boron compound represented by formula (8), $$ArB(Or^e)_2 \quad (8)$$

[wherein Ar has the same meaning as above, and $r^e$ represents a hydrogen atom or C1-C8 alkyl, or $r^e$s together represent a cyclic dialkoxy group such as a pinacol group], to act on compound (3') in the presence of a palladium catalyst and a base in an appropriate solvent to obtain a compound (3").

The amount of boron compound represented by formula (8) is 2.0 to 10.0 times, preferably, 2.1 to 5.0 times, more preferably 2.5 to 3.5 times the molar amount of compound (3').

As a palladium catalyst, a zero-valent palladium complex such as bis[1,2-(diphenylphosphino)ethane]palladium, bis(dibenzylideneacetone)palladium, tris(dibenzylideneacetone)dipalladium, and Pd(PPh$_3$)$_4$ can be preferably used in a 0.005 to 0.2 equivalent amount, preferably, 0.001 to 0.1 equivalent amount, and more preferably, 0.01 to 0.05 equivalent amount, with respect to compound (3').

Further, the palladium catalyst can also be prepared and used in the reaction system by allowing phosphine to act on a divalent palladium compound. Examples of the divalent palladium include a palladium halide such as palladium chloride and palladium bromide; palladium acetate; and palladium acetoacetate, and a preferred example is palladium acetate. Phosphine is not particularly limited, and readily accessible triarylphosphines can be preferably used, and triphenylphosphine is more preferred. The molar ratio of the divalent palladium compound and phosphine is 1:1 to 1:10, and preferably 1:2 to 1:5.

As for a base, the followings can be used appropriately: lithium hydroxide, sodium hydroxide, sodium hydrogen carbonate, sodium methoxide, sodium ethoxide, potassium hydroxide, potassium carbonate, potassium methoxide, potassium ethoxide, sodium tert-butoxide, potassium tert-butoxide, cesium hydroxide, cesium carbonate, thallium hydroxide, and phosphates, i.e., disodium phosphate, trisodium phosphate, and hydrate thereof, dipotassium phosphate, tripotassium phosphate and hydrate thereof, sodium pyrophosphate and hydrate thereof, potassium pyrophosphate and hydrate thereof, etc. A preferred base is tripotassium phosphate or hydrate thereof, the amount of which is 2.0 to 10.0 times, preferably, 2.1 to 5.0 times, and more preferably 2.5 to 3.5 times the molar amount of compound (3').

As for a solvent, the followings can be preferably used: an aromatic solvent such as benzene, toluene, and xylene; an ether solvent such as ether, isopropyl ether, THF, tent-butyl methyl ether, and CPME; an amide solvent such as DMF, N-methylpyrrolidine-2-one (NMP), and N,N'-dimethylimidazolidine-2-one (DMI). The amount of the solvent (L) is 1.0 to 100 times, and more preferably 3 to 30 times larger with respect to compound (3') (kg) in terms of volume (L)/weight (kg).

The reaction is performed at an appropriate temperature from the melting point to the boiling point of the solvent, preferably at 0° C. to 120° C., and more preferably at room temperature to 100° C.

The reaction is performed by stirring. The reaction time can be appropriately set according to the reaction rate, and is preferably 3 to 50 hours, and more preferably 6 to 24 hours.

Step 2 comprises allowing a halogenating agent, and optionally a reaction initiator, to act on compound (3") so that it can be lead to compound (3''') in an appropriate solvent.

As a halogenating agent, chlorine, N-chlorosuccinimide, bromine, N-bromosuccinimide (NBS), etc. and iodine, etc. can be used. A preferred halogenating agent is NBS, and the amount is preferably 2.0 to 5.0 times, and more preferably 2.1 to 3.0 times the molar amount of compound (3").

As a reaction initiator, radical reaction initiators such as AIBN and BPO (benzoyl peroxide) are preferably used, and the amount of which is 0.05 to 1.0 times, and more preferably, 0.1 to 0.5 times the molar amount of compound (3").

Solvent is not particularly limited as long as it does not inhibit the reaction, and the followings can be used: a hydrocarbon solvent such as hexane, cyclohexane, and benzene; a chlorine solvent such as methylene chloride, chloroform, and chlorobenzene; an amide solvent such as DMF, N-methylpyrrolidine-2-one (NMP), and N,N'-dimethylimidazolidine-2-one (DMI). The amount of solvent (L) is preferably 1.0 to 100 times, and more preferably 3 to 30 times larger with respect to compound (3') (kg) in terms of volume (L)/weight (kg).

The reaction is performed at an appropriate temperature from the melting point to the boiling point of the solvent, and preferably at 0° C. to 100° C.

The reaction is performed by stirring. The reaction time can be appropriately set according to the reaction rate, which is preferably 3 to 50 hours, and more preferably 6 to 24 hours.

Step 3 comprises allowing amine compound represented by formula (9), $$HNR^{3'}R^{4'} \quad (9)$$

(wherein $R^{3'}$ and $R^{4'}$ have the same meaning as above), to act on compound (3''') in the presence of a base in an appropriate solvent to obtain a compound (1a).

The amount of the amine compound represented by formula (9) is 0.5 to 5.0 times, and preferably 0.75 to 2.0 times the molar amount of compound (3''').

As for a base, the followings can be used preferably: an inorganic base such as lithium hydroxide, sodium hydroxide, sodium hydrogen carbonate, sodium methoxide, sodium ethoxide, potassium hydroxide, potassium carbonate, potassium methoxide, potassium ethoxide, potassium tert-butoxide, cesium hydroxide, and cesium carbonate. The amount of the base is 2 to 30 times, and preferably, 3 to 20 times the molar amount of compound (3').

The solvent is not particularly limited as long as it does not inhibit the reaction, and the followings can be used: a hydrocarbon solvent such as hexane, cyclohexane, benzene and toluene; a chlorine solvent such as methylene chloride, chloroform, and chlorobenzene; a nitrile solvent such as acetonitrile and bezonitrile; and an amide solvent such as DMF, N-methylpyrrolidine-2-one (NMP), and N,N'-dimethylimidazolidine-2-one (DMI). The amount of solvent (L) is preferably 1.0 to 100 times, and more preferably 3 to 30 times larger with respect to a compound (3') (kg) in terms of volume (L)/weight (kg).

It is also possible to perform the reaction under phase-transfer reaction conditions, and in this case, the reaction is performed by allowing a common phase-transfer catalyst such as tetrabutylammonium bromide, benzyltrimethylammonium bromide, benzyltriethylammonium bromide, 18-crown-6-ether, and 15-crown-4-ether to co-exist in an amount 0.005 to 0.2 times, and preferably 0.01 to 0.05 times the molar amount of compound (3'''). In this case, the above-mentioned base can be used as an aqueous solution or as it is in a solid form.

The reaction is performed by stirring at an appropriate temperature from the melting point to the boiling point of the solvent, preferably at room temperature to 100° C. The reaction time can be appropriately set according to the reaction rate, and is preferably 3 to 50 hours, and more preferably 6 to 24 hours.

2-1. Optically Active Biphenyl Derivative

In order to prepare the above azepine derivative, an optically active biphenyl derivative represented by the following formula (3),

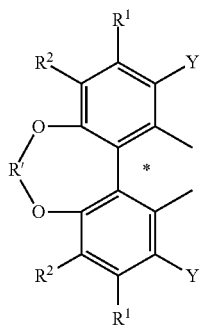

is used.

In the optically active biphenyl derivative, R', $R^1$ and $R^2$ have the same meaning as above (however, a preferred halogen atom is chlorine, bromine, or iodine); * have the same meaning as above; and Y represents a sulfonate group or a halogen atom.

In this context, —O—R'—O— is preferably a divalent substituent wherein $r^1$ is an oxygen atom in formulae (4-1) to (4-22) and (5-1) and (5-2) exemplified as Rs, and is more preferably the divalent groups selected from the above-mentioned group and shown in the followings, wherein $r^1$ is an oxygen atom:

(4-1), (4-2), (4-3), (4-4), (4-6), (4-7), (4-9), (4-12), (4-13), (4-17), (4-20), (5-1), and (5-2).

The sulfonate group of Y is a group represented by formula (7),

wherein a preferred $r^c$ is a linear, branched, or cyclic C1-C8 alkyl group, or C6-C14 aryl group that may have a substituent.

In this context, the "linear, branched, or cyclic C1-C8 alkyl group" encompasses methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, cyclopentyl, etc.

The "C6-C14 aryl group" of a "C6-C14 aryl group that may have a substituent" encompasses phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 10-phenanthryl, azulenyl, indenyl, indanyl, tetralinyl, etc.

Examples of the "substituent" in the phrase "that may have a substituent" include:

a halogen atom such as fluorine, chlorine, bromine and iodine;

a linear, branched, or cyclic C1-C8 alkyl group such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl, among which more preferred examples of the alkyl group include a linear, branched, or cyclic C1-C8 alkyl group wherein at the α position, there is a secondary or tertiary carbon, such as isopropyl, sec-butyl, tert-butyl, tert-pentyl, tert-hexyl, tert-heptyl, tert-octyl, cyclopropyl, cyclobutyl, and cyclopentyl; and a linear, branched, or cyclic C1-C8 alkoxy group such as methoxy, ethoxy, propoxy, isopropoxy, butoxy, isobutoxy, sec-butoxy, tent-butoxy, pentyloxy, isopentyloxy, hexyloxy, heptyloxy, octyloxy, cyclopropoxy, cyclobutoxy, 2 methylcyclopropoxy, cyclopropylmethoxy, and cyclopentyloxy.

Further, the hydrogen atom of each group in the above group of substituents may be appropriately substituted by a fluorine atom.

2-2. Method for Preparing Optically Active Biphenyl Derivative

An optically active biphenyl derivative represented by the above formula (3) can be prepared by the method represented by the following reaction formula (E),

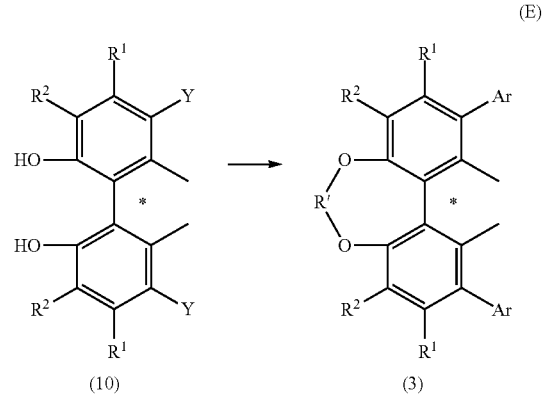

(wherein —O—R'—O—, $R^1$, $R^2$, Ar, and * have the same meaning as above).

Specifically, it is a step of allowing a bifunctional compound represented by formula (11),

(wherein R' is a divalent group having the same meaning as above, and x2 represents a leaving group), to act on an optically active biphenyl derivative represented by formula (10) in the presence of a base in an appropriate solvent to obtain a compound (3).

R' in the bifunctional compound represented by formula (11) is preferably the part where $r^1$ has been excluded from formulae (4-1) to (4-22) and (5-1) to (5-4) exemplified as Rs, and among which, R's corresponding to (4-1), (4-2), (4-3), (4-4), (4-6), (4-7), (4-9), (4-12), (4-13), (4-16), (4-17), (5-1), (5-2), (5-3), and (5-4) are particularly preferred.

The two ×2s in the bifunctional compound represented by formula (11) are leaving groups. These two groups may be the same or different, and are not particularly limited as long as they are substituents that can be commonly used as leaving groups in a chemical reaction. Preferred examples include a halogen atom such as chlorine, bromine, and iodine, and a sulfonyloxy group represented by formula (C'),

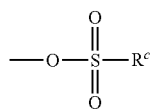
(C')

(wherein $R^c$ is preferably a linear, branched, or cyclic C1-C8 alkyl group that may have a substituent, C6-C14 aryl group that may have a substituent, C3-C8 heteroaryl group that may have a substituent, or C7-C16 aralkyl group that may have a substituent). More preferred examples of the halogen atom include chlorine, bromine, and iodine, and examples of the sulfonyloxy group represented by formula (C') include methanesulfonyloxy, benzenesulfonyloxy, toluenesulfonyloxy, and trifluoromethanesulfonyloxy, since these are readily accessible.

In this context, the "linear, branched, or cyclic C1-C8 alkyl group" of a "linear, branched, or cyclic C1-C8 alkyl group that may have a substituent" encompasses methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, cyclopentyl, etc.

The "C6-C14 aryl group" of a "C6-C14 aryl group that may have a substituent" encompasses phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 10-phenanthryl, azulenyl, indenyl, indenyl, tetralinyl, etc.

The "C3-C8 heteroaryl group" of a "C3-C8 heteroaryl group that may have a substituent" encompasses 2-pyridyl, 3-pyridyl, 4-pyridyl, 2-quinolyl, 3-quinolyl, 4-quinolyl, 5-quinolyl, 6-quinolyl, 7-quinolyl, 8-quinolyl, 2-indolyl, 3-indolyl, 4-indolyl, 5-indolyl, 6-indolyl, 7-indolyl, 2-furyl, 3-furyl, 2-thienyl, 3-thienyl, 2-pyrrolidyl, 3-pyrrolidyl, 2-imidazolyl, 4-imidazolyl, 5-imidazolyl, 2-oxazolyl, 4-oxazolyl, 5-oxazolyl, 2-thiazolyl, 4-thiazolyl, 5-thiazolyl, tetrahydro-2-furanyl, tetrahydro-2-pyranyl, etc.

The "C7-C16 aralkyl group" of a "C7-C16 aralkyl group that may have a substituent" encompasses benzyl, 2-phenylethyl, 1-naphthylmethyl, 2-naphthylmethyl, etc.

Examples of the "substituent" in the phrase "that may have a substituent" encompasses the followings:
a halogen atom such as fluorine, chlorine, bromine and iodine;
a linear, branched, or cyclic C1-C8 alkyl group such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl, among which more preferred examples of the alkyl group include a linear, branched, or cyclic C1-C8 alkyl group wherein at the α position, there is a secondary or tertiary carbon, such as isopropyl, sec-butyl, tert-butyl, tert-pentyl, tert-hexyl, tert-heptyl, tert-octyl, cyclopropyl, cyclobutyl, and cyclopentyl; and
a linear, branched, or cyclic C1-C8 alkoxy group such as methoxy, ethoxy, propoxy, isopropoxy, butoxy, isobutoxy, sec-butoxy, tert-butoxy, pentyloxy, isopentyloxy, hexyloxy, heptyloxy, octyloxy, cyclopropoxy, cyclobutoxy, 2-methylcyclopropoxy, cyclopropylmethoxy, and cyclopentyloxy.

An optically active biphenyl derivative represented by formula (3) can be obtained by allowing a bifunctional compound represented by formula (11) to act on an optically active biphenyl derivative represented by formula (10) in the presence of a base in an appropriate solvent.

The amount of the bifunctional compound represented by formula (11) is 1.0 to 5.0 times, and preferably 1.05 to 2.0 times the molar amount of an optically active biphenyl derivative represented by formula (10).

As for a base, the followings can be used preferably: inorganic bases such as lithium hydroxide, sodium hydroxide, sodium hydrogen carbonate, sodium methoxide, sodium ethoxide, potassium hydroxide, potassium carbonate, potassium methoxide, potassium ethoxide, potassium tert-butoxide, cesium hydroxide, and cesium carbonate. The amount of the base is 2 to 30 times, and preferably 3 to 20 times the molar amount of compound (10).

Solvent is not particularly limited as long as it does not inhibit the reaction, and the followings can be used: a hydrocarbon solvent such as hexane, cyclohexane, benzene, and toluene; a chlorine solvent such as methylene chloride, chloroform, and chlorobenzene; a nitrile solvent such as acetonitrile and benzonitrile; a ketone solvent such as acetone, ethyl methyl ketone, and tert-butyl methyl ketone; an amide solvent such as DMF, N-methylpyrrolidine-2-one (NMP), and N,N'-dimethylimidazolidine-2-one (DMI); and DMSO. The amount of solvent (L) is preferably 1.0 to 100 times, and more preferably 5 to 30 times larger with respect to an optically active biphenyl compound (kg) represented by formula (10) in terms of volume (L)/weight (kg).

It is also possible to perform the reaction under phase-transfer reaction conditions, and in this case, the reaction is performed by allowing a common phase-transfer catalyst such as tetrabutylammonium bromide, benzyltrimethylammonium bromide, benzyltriethylammonium bromide, 18-crown-6-ether, and 15-crown-4-ether to co-exist in an amount 0.005 to 0.2 times, and preferably 0.01 to 0.05 times the molar amount of an optically active biphenyl compound represented by formula (10). In this case, the above-mentioned base can be used as an aqueous solution or as it is in a solid form.

The reaction is performed by stirring at an appropriate temperature from the melting point to the boiling point of the solvent, preferably at 0° C. to 80° C. The reaction time can be appropriately set according to the reaction rate, and is preferably 3 to 50 hours, and more preferably 6 to 24 hours.

3. Method for Preparing Optically Active α,α-Disubstituted Glycine Derivative or Optically Active α-Monosubstituted Glycine Derivative The following reaction can be performed in the presence of an optically active 6,7-dihydro-5H-dibenzo[c,e]azepine derivative of the present invention.

An optically active α,α-disubstituted glycine derivative represented by formula (B),

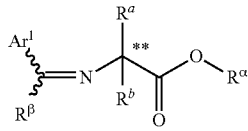
(B)

(wherein $R^\alpha$ represents a linear, branched, or cyclic C1-C8 alkyl group that may have a substituent, C6-C14 aryl group that may have a substituent, C3-C8 heteroaryl group that may have a substituent, or C7-C16 aralkyl group that may have a substituent;

$R^\beta$ represents a hydrogen atom, linear, branched, or cyclic C1-C8 alkyl group, C6-C14 aryl group that may have a substituent, or C7-C16 aralkyl group that may have a substituent;

$R^a$ represents an organic group;

$R^b$ represents an organic group that is different from $R^a$;

Ar' represents a C6-C14 aryl group that may have a substituent;

** represents optical activity, i.e., that of two types of mirror-image isomers, one isomer is present in excess of the other isomer); and bond axes shown by wavy lines represent that the configuration of a substituent on a carbon atom replaced by these bond axes is not limited)

is prepared by reacting an α-substituted glycine derivative represented by the following formula (A),

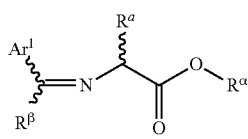
(A)

(wherein $R^\alpha$, $R^\beta$, $R^a$, Ar' and bond axes shown by the wavy lines have the same meaning as above), with a compound of the following formula (C), $R^b Z$ (C)

(wherein $R^b$ has the same meaning as above, and Z represents a leaving group).

Specifically, it is a method for preparing an optically active α,α-disubstituted glycine derivative from an α-substituted glycine derivative, represented by the following reaction formula (X).

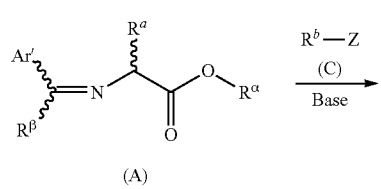
(X)

-continued

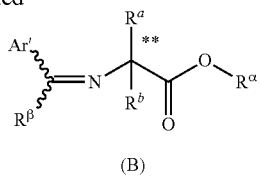
(B)

Further, the following reaction can also be performed in the presence of an optically active 6,7-dihydro-5H-dibenzo[c,e]azepine derivative of the present invention.

An optically active α-monosubstituted glycine derivative represented by the following formula (B'),

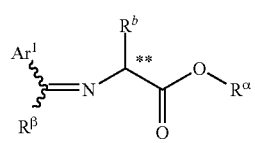
(B')

(wherein $R^\alpha$, $R^\beta$, $R^b$, Ar' **, and bond axes shown by the wavy lines are the same as defined above)

is prepared by reacting an glycine derivative represented by the following formula (A'),

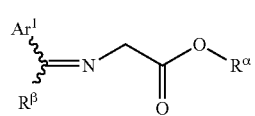
(A')

(wherein $R^\alpha$, $R^\beta$, and Ar' are the same as defined above), with a compound of the following formula (C), $R^b Z$ (C)

(wherein $R^b$ and Z are the same as defined above).

Specifically, it is a method for preparing an optically active α-monosubstituted glycine derivative from a glycine derivative, represented by the following reaction formula (X').

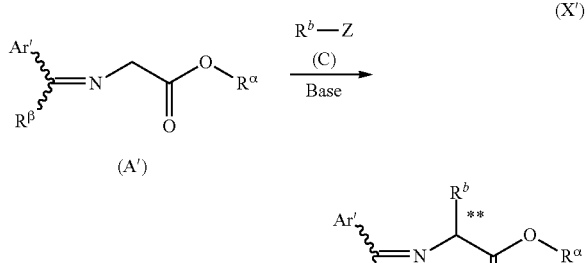
(X')

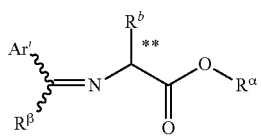
(B')

In the above reaction formulae, each substituent is defined as follows.

The "linear, branched, or cyclic C1-C8 alkyl group" of a "linear, branched, or cyclic C1-C8 alkyl group that may have a substituent" of $R^\alpha$ encompasses methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, cyclopentyl, etc.

The "C6-C14 aryl group" of a "C6-C14 aryl group that may have a substituent" encompasses phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 10-phenanthryl, azulenyl, indenyl, indanyl, tetralinyl, etc.

The "C3-C8 heteroaryl group" of a "C3-C8 heteroaryl group that may have a substituent" encompasses 2-pyridyl, 3-pyridyl, 4-pyridyl, 2-quinolyl, 3-quinolyl, 4-quinolyl, 5-quinolyl, 6-quinolyl, 7-quinolyl, 8-quinolyl, 2-indolyl, 3-indolyl, 4-indolyl, 5-indolyl, 6-indolyl, 7-indolyl, 2-furyl, 3-furyl, 2-thienyl, 3-thienyl, 2-pyrrolidyl, 3-pyrrolidyl, 2-imidazolyl, 4-imidazolyl, 5-imidazolyl, 2-oxazolyl, 4-oxazolyl, 5-oxazolyl, 2-thiazolyl, 4-thiazolyl, 5-thiazolyl, tetrahydro-2-furanyl, tetrahydro-2-pyranyl, etc.

The "C7-C16 aralkyl group" of a "C7-C16 aralkyl group that may have a substituent" encompasses benzyl, 2-phenylethyl, 1-naphthylmethyl, 2-naphthylmethyl, etc.

Examples of the "substituent" in the phrase "that may have a substituent" include the followings:
a halogen atom such as fluorine, chlorine, bromine and iodine;
a linear, branched, or cyclic C1-C8 alkyl group such as methyl, ethyl, propyl, isopropyl, butyl, isobutyl, sec-butyl, tent-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl, and more preferred examples of the alkyl group include a linear, branched, or cyclic C1-C8 alkyl group wherein at the α position, there is a secondary or tertiary carbon, such as isopropyl, sec-butyl, tert-butyl, tert-pentyl, tert-hexyl, tert-heptyl, tert-octyl, cyclopropyl, cyclobutyl, and cyclopentyl; and
a linear, branched, or cyclic C1-C8 alkoxy group such as methoxy, ethoxy, propoxy, isopropoxy, butoxy, isobutoxy, sec-butoxy, tert-butoxy, pentyloxy, isopentyloxy, hexyloxy, heptyloxy, octyloxy, cyclopropoxy, cyclobutoxy, 2-methylcyclopropoxy, cyclopropylmethoxy, and cyclopentyloxy.

The definitions for a "linear, branched, or cyclic C1-C8 alkyl group", "C6-C14 aryl group that may have a substituent", and "C7-C16 aralkyl group that may have a substituent" at $R^\beta$ are the same as those defined in $R^5$, and as for $R^6$, a hydrogen atom or linear C1-C6 lower alkyl group is preferred.

The "C6-C14 aryl group" of a "C6-C14 aryl group that may have a substituent" at Ar' is the same as defined above.

Further, an example of the "substituent" of a "C6-C14 aryl group that may have a substituent" is a substituent on a benzene ring, and the number of which is singular or plural, and the type of the substituent is the same or different, and the position of the substitution is not particularly limited. Examples of a preferred substituent include the followings, since they are readily accessible:
a halogen atom such as fluorine, chlorine, bromine and iodine:
a linear, branched, or cyclic C1-C8 alkyl group such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl;
a linear, branched, or cyclic C1-C8 alkoxy group such as methoxy, ethoxy, propoxy, isopropoxy, butoxy, isobutoxy, sec-butoxy, tert-butoxy, pentyloxy, isopentyloxy, hexyloxy, heptyloxy, octyloxy, cyclopropoxy, cyclobutoxy, 2-methylcyclopropoxy, cyclopropylmethoxy, and cyclopentyloxy;
a cyano group;
a nitro group, etc.

$R^a$ and $R^b$ are organic groups that are different from each other, and a linear, branched, or cyclic C1-C8 alkyl group that may have a substituent or C7-C16 aralkyl group that may have a substituent can be preferably applied and used with no particular limitation.

In this context, the "linear, branched, or cyclic C1-C8 alkyl group" of a "linear, branched, or cyclic C1-C8 alkyl group that may have a substituent" encompasses methyl, ethyl, propyl, isopropyl, butyl, isobutyl, sec-butyl, tent-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, cyclopentyl, etc.

The "C7-C16 aralkyl group" of a "C7-C16 aralkyl group that may have a substituent" encompasses benzyl, 2-phenylethyl, 1-naphthylmethyl, 2-naphthylmethyl, etc.

Examples of the substituent in the above phrase "that may have a substituent" encompass the followings:
a halogen atom such as fluorine, chlorine, bromine and iodine;
a linear, branched, or cyclic C1-C8 alkyl group such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, cyclopropyl, cyclobutyl, 2-methylcyclopropyl, cyclopropylmethyl, and cyclopentyl, and these groups having a substituent;
a C2-C8 alkenyl group such as vinyl, 1-propenyl, 2-propenyl, isopropenyl, 1-butenyl, 2-butenyl, 3-butenyl, 1-pentenyl, 2-pentenyl, 3-pentenyl, 4-pentenyl, 1-methyl-2-butenyl, 1-methyl-3-butenyl, 1,1-dimethyl-2-propenyl, 3-methyl-2-butenyl, 1-hexenyl, 2-hexenyl, 3-hexenyl, 4-hexenyl, 5-hexenyl, 2-methyl-1-pentenyl, 3-methyl-1-pentenyl, 4-methyl-1-pentenyl, 2-methyl-2-pentenyl, 3-methyl-2-pentenyl, 2-ethyl-1-butenyl, 3,3-dimethyl-1-butenyl, 1-heptenyl, 2-heptenyl, 3-heptenyl, 1-octenyl, 2-octenyl, 3-octenyl, and 4-octenyl, and these groups having a substituent;
a C2-C8 alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 4-methyl-1-pentynyl, 1-hexynyl, and 1-octynyl, and these groups having substituent; and
a C1-C8 alkoxy group such as methoxy, ethoxy, propoxy, isopropoxy, butoxy, isobutoxy, sec-butoxy, tert-butoxy, pentyloxy, isopentyloxy, hexyloxy, heptyloxy, octyloxy, cyclopropoxy, cyclobutoxy, 2-methylcyclopropoxy, cyclopropylmethoxy, cyclopentyloxy, methylenedioxy, and ethylenedioxy, and these groups having a substituent;
a C6-C14 aryl group such as phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, and 10-phenanthryl, and these groups having a substituent;
a C3-C8 heteroaryl group such as 2-pyridyl, 3-pyridyl, 4-pyridyl, 2-quinolyl, 3-quinolyl, 4-quinolyl, 5-quinolyl, 6-quinolyl, 7-quinolyl, 8-quinolyl, 2-indolyl, 3-indolyl, 4-indolyl, 5-indolyl, 6-indolyl, 7-indolyl, 2-furyl, 3-furyl, 2-thienyl, 3-thienyl, 2-pyrrolidyl, 3-pyrrolidyl, 2-imidazolyl, 4-imidazolyl, 5-imidazolyl, 2-oxazolyl, 4-oxazolyl, 5-oxazolyl, 2-thiazolyl, 4-thiazolyl, 5-thiazolyl, tetrahydro-2-furanyl, and tetrahydro-2-pyranyl, and these groups having a substituent;
oxo group, nitro group, and cyano group.

The substituent of the above phrase "having a substituent" can be defined as the same substituents as the above substituents.

Z is a leaving group and is not particularly limited as long as it is a substituent that can be used as a leaving group in a chemical reaction. Generally, a halogen atom such as chlorine, bromine, and iodine, and a sulfonyloxy group represented by the above formula (C') are preferred, and more preferred examples of the halogen atom include chlorine, bromine, and iodine. Examples of the sulfonyloxy group represented by the above formula (C') are methanesulfonyloxy, benzenesulfonyloxy, toluenesulfonyloxy, and trifluoromethanesulfonyloxy, since these are readily accessible.

The reaction is performed under phase-transfer reaction conditions, with a two solution-two phase system of an organic solvent and a basic solution, or with a one-solution-two phase system wherein a single base has been dispersed and made to become a slurry in an organic solvent. An optically active 6,7-dihydro-5H-dibenzo[c,e]azepine derivative represented by formula (1') (hereinafter, referred to as the azepine derivative represented by formula (1')) is used as a phase-transfer catalyst.

The molar ratio of an α-substituted glycine derivative represented by formula (A) or a glycine derivative represented by formula (A') to the azepine derivative represented by formula (1') is 20,000/1 to 10/1, preferably 10,000/1 to 100/1, and more preferably 5,000/1 to 500/1.

The molar ratio of an α-substituted glycine derivative represented by formula (A) or a glycine derivative represented by formula (A') to a compound of formula (C) is 1/0.75 to 1/10, preferably 1/1 to 1/5, and more preferably 1/1.1 to 1/2.

The molar ratio of an α-substituted glycine derivative represented by formula (A) or a glycine derivative represented by formula (A') to a base is 1/1 to 1/100, preferably 1/1 to 1/10, and more preferably 1/1.1 to 1/3. As the base, an inorganic base such as lithium hydroxide, sodium hydroxide, sodium hydrogen carbonate, sodium methoxide, sodium ethoxide, potassium hydroxide, potassium carbonate, potassium methoxide, potassium ethoxide, potassium tert-butoxide, cesium hydroxide, and cesium carbonate can be used alone or in combination. When the base is used as an aqueous solution, its concentration (w/w) is adjusted appropriately from 5% to supersaturation, while the preferred concentration is from 10% to saturation concentration.

As for a solvent, when the reaction is performed with a two solution-two phase system, it is preferred to use a non-water soluble solvent such as a hydrocarbon solvent including hexane, cyclohexane, benzene, and toluene, and a chlorine solvent including methylene chloride, chloroform, and chlorobenzene, alone or in combination. More preferably, a hydrocarbon solvent such as hexane, cyclohexane, benzene, and toluene can be used alone or as a mixed solvent. When the reaction is performed with a one solution-two phase system, a nitrile solvent such as acetonitrile and benzonitrile, an amide solvent such as DMF, N-methylpyrrolidine-2-one (NMP), and N,N'-dimethylimidazolidine-2-one (DMI), etc, can be used in addition to the above solvents. The amount of the solvent (L) is preferably 1.0 to 100 times, and more preferably 5 to 30 times larger with respect to an α-substituted glycine derivative represented by formula (A) or a glycine derivative represented by formula (A') (kg) in terms of volume (L)/weight (kg).

Commonly, any of the above organic solvents is used, but it is also possible to perform the reaction with a basic aqueous solution only, without using an organic solvent.

The reaction is performed by stirring at an appropriate temperature from the melting point to the boiling point of the solvent, preferably at −10° C. to 60° C. The reaction time can be appropriately set according to the reaction rate, and is preferably 3 to 60 hours, and more preferably 6 to 24 hours.

EXAMPLES

The present invention will be further explained in detail in the following by referring to the Examples, while the present invention will not be limited to these Examples.

Example 1

Synthesis of Optically Active 6,7-dihydro-5H-dibenzo[c,e]azepine derivative
Example 1-1

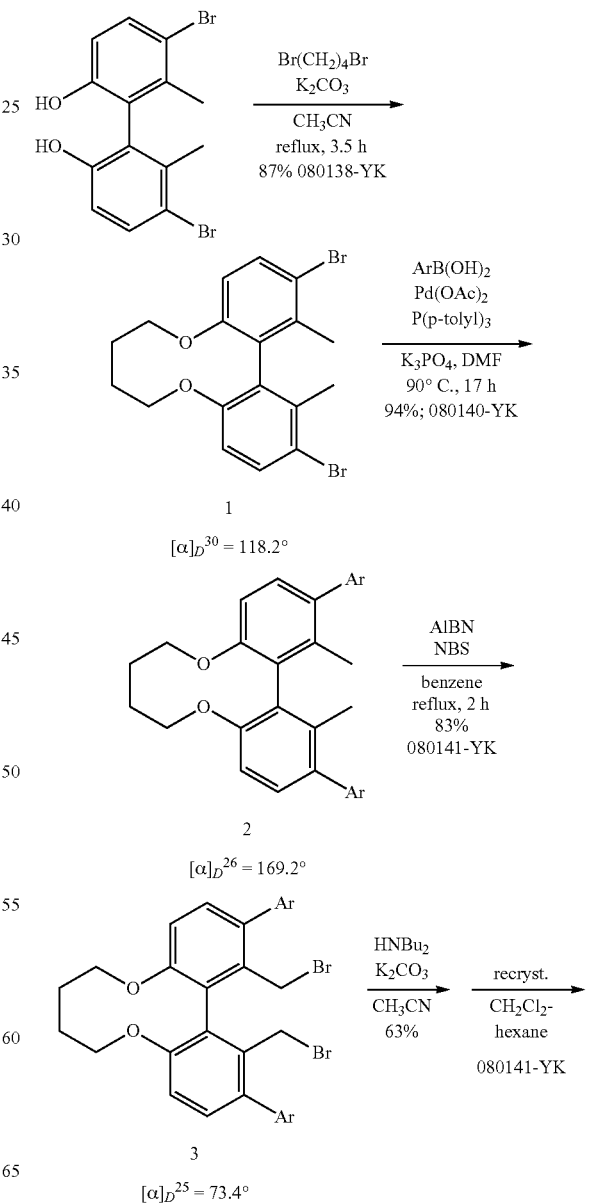

-continued

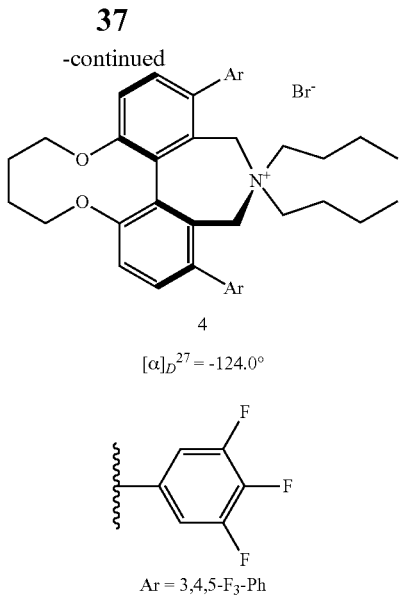

4

$[\alpha]_D^{27} = -124.0°$

Ar = 3,4,5-F$_3$-Ph

Step 1. Synthesis of (5)-1

Chiral bisphenol (0.5 mmol) and potassium carbonate base (1.5 to 2 mmol) were dissolved in an acetonitrile (50 mL) solvent. 1,4-dibromobutane was slowly added dropwise to the mixture while being refluxed. After 3 hours, acetonitrile was removed by distillation under reduced pressure, which was followed by extraction and drying. After concentrated under reduced pressure, the resultant was subjected to a simple purification using a silica-gel short column, and used for the next step (yield 87%).

$^1$H NMR (300 MHz, CDCl$_3$) δ 7.51 (2H, d, J=8.7 Hz, ArH), 6.84 (2H, d, J=8.7 Hz, ArH), 4.30-4.38 (2H, m, ArOCH$_2$), 3.90-3.99 (2H, m, ArOCH$_2$), 2.07 (6H, s, ArCH$_3$), 1.61-1.79 (4H, m, CH$_2$); $[\alpha]_D^{29}$+118.2° (c 1.0, CHCl$_3$).

Step 2. Synthesis of (S)-2

Aryl bromide derivative (S)-1 was subjected to Suzuki coupling with aryl boronic acid (1.5 mmol) under an argon atmosphere in the presence of palladium acetate (5 mol %) and p-tolyltriphenylphosphine (20 mol %) catalysts, in a DMF (5 mL) solvent using potassium phosphate (5 e.g.) as a base. The reaction mixture was stirred at 90° C. for 12 hours. After the reaction was completed, the resultant was filtered using celite, then extracted and dried. After concentrated under reduced pressure, the resultant was purified by column chromatography (hexane:ethyl acetate=10:1) and used for the text step (yield 94%).

$^1$H NMR (300 MHz, CDCl$_3$) δ 7.15 (2H, d, J=8.7 Hz, ArH), 6.90-7.03 (6H, m, ArH), 4.40-4.48 (2H, m, ArOCH$_2$), 3.95-4.07 (2H, m, ArOCH$_2$), 1.94 (6H, s, ArCH$_3$), 1.74-2.02 (4H, m, CH$_2$); $[\alpha]_D^{26}$+169.20° (c 1.0, CHCl$_2$).

Step 3. Synthesis of (S)-3

To the obtained (S)-2, NBS (2.2 e.g.) and AIBN (10 mol %) were added, and in a benzene solvent (20 mL), the mixture was stirred for 3 hours while being refluxed. After the reaction was completed, the resultant was extracted, dried and concentrated under reduced pressure, and then purified by column chromatography (hexane:ethyl acetate=15:1) (yield 83%).

$^1$H NMR (300 MHz, CDCl$_3$) δ 7.12-7.28 (8H, m, ArH), 4.48 (2H, d, J=12.0 Hz, ArOCH$_2$), 4.09-4.20 (4H, m, ArCH$_2$Br), 3.90-4.01 (2H, m, ArOCH$_2$), 1.60-1.90 (4H, m, CH$_2$); $[\alpha]_D^{25}$+73.4° (c 1.0, CHCl$_3$).

Step 4. Synthesis of (S)-4

To bis-bromide (S)-3 which is a catalyst precursor, an excessive amount (2 to 3 times the molar amount of bis-bromide (S)-3) of n-dibutylamine was added, and the resultant mixture was stirred at 40° C. for 3 hors in the presence of potassium carbonate (2 to 3 times the molar amount of bis-bromide (S)-3) in an acetonitrile solvent. Completion of the reaction was confirmed by TLC, and then the resultant was extracted, dried, and concentrated, and then purified by column chromatography (methylene chloride:methanol=10:1) (yield 63%).

$^1$H NMR (300 MHz, CDCl$_3$) δ 6.90-7.53 (4H, m, ArH), 7.40 (2H, d, J=8.7 Hz, ArH), 7.32 (2H, d, J=8.7 Hz, ArH), 4.76 (2H, d, J=13.8 Hz, ArCH$_2$N), 4.54-4.59 (2H, m, ArOCH$_2$), 4.20-4.35 (2H, m, ArOCH$_2$), 3.66 (2H, d, J=13.8 Hz, ArCH$_2$N), 3.22 (2H, t, J=12.9 Hz, NCH$_2$), 2.70-2.85 (2H, m, NCH$_2$), 0.87-2.15 (10H, m, CH$_2$), 0.75 (6H, t, J=6.9 Hz, CH$_3$), 0.20-0.31 (2H, m, CH$_2$); $[\alpha]_D^{27}$−124.40° (c 1.0, MeOH).

Example 1-2

Compound of Example 1-2 was synthesized in the same manner as Example 1-1.

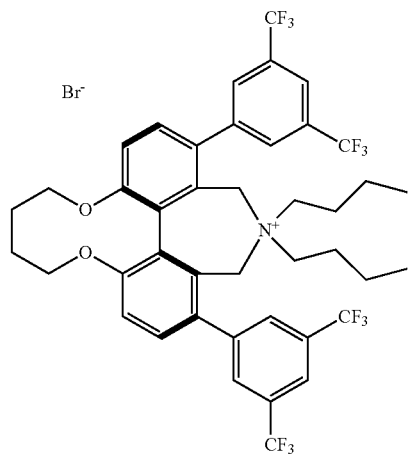

$^1$H NMR (300 MHz, CDCl$_3$) δ 7.62-8.30 (6H, br, ArH), 7.47 (2H, d, J=8.7 Hz, ArH), 7.39 (2H, d, J=8.7 Hz, ArH), 4.45-4.66 (2H, m, ArOCH$_2$), 4.55 (2H, d, J=13.8 Hz, ArCH$_2$N), 4.33 (2H, t, J=9.3 Hz, ArOCH$_2$), 3.94 (2H, d, J=13.8 Hz, ArCH$_2$N), 3.20-3.38 (2H, m, NCH$_2$), 2.62-2.80 (2H, m, NCH$_2$), 1.82-2.15 (4H, m, CH$_2$), 0.55-1.65 (12H, m, CH$_2$, CH$_3$), 0.16-0.35 (2H, m, CH$_2$); $[\alpha]_D^{26}$−72.9° (c 1.0, MeOH).

Example 1-3

Compound of Example 1-3 was synthesized in the same manner as Example 1-1.

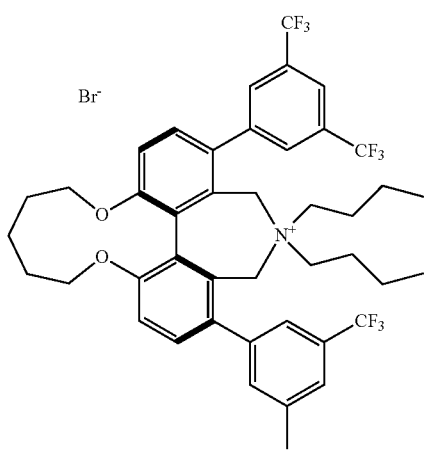

¹H NMR (300 MHz, CDCl₃) δ 7.72-8.25 (6H, br, ArH), 7.45 (2H, d, J=8.7 Hz, ArH), 7.30 (2H, d, J=8.7 Hz, ArH), 4.45-4.62 (4H, m, ArOCH₂, ArCH₂N), 4.18-4.30 (2H, m, ArOCH₂), 3.91 (2H, d, J=13.8 Hz, ArCH₂N), 3.21 (2H, t, J=12.0 Hz, NCH₂), 2.60-2.78 (2H, m, NCH₂), 1.66-1.99 (6H, m, CH₂), 0.52-1.15 (12H, m, CH₂, CH₃), 0.15-0.29 (2H, m, CH₂); $[\alpha]_D^{29}$ −50.8° (c 1.0, CHCl₃).

Example 1-4

Compound of Example 1-4 was synthesized in the same manner as Example 1-1.

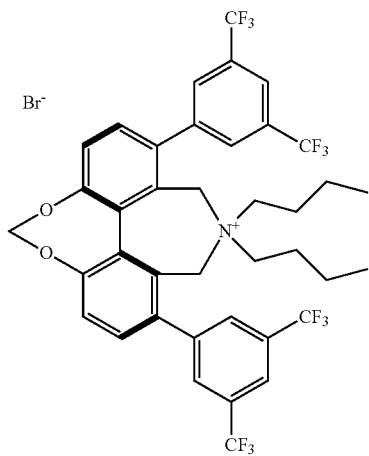

¹H NMR (300 MHz, CDCl₃) δ 7.79-8.41 (6H, br, ArH), 7.58 (2H, d, J=8.7 Hz, ArH), 7.53 (2H, d, J=8.7 Hz, ArH), 5.75 (2H, s, ArOCH₂O), 4.59 (2H, d, J=14.1 Hz, ArCH₂N), 4.11 (2H, d, J=14.1 Hz, ArNCH₂), 3.28-3.44 (2H, m, NCH₂), 2.72-2.88 (2H, m, NCH₂), 0.20-1.45 (14H, m, CH₂, CH₃); $[\alpha]_D^{29}$ +4.4° (c 0.5, MeOH).

Example 1-5

Compound of Example 1-5 was synthesized in the same manner as Example 1-1.

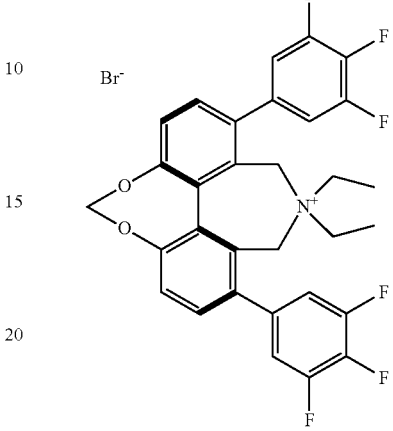

¹H NMR (300 MHz, CDCl₃) δ 7.50 (2H, d, J=8.4 Hz, ArH), 7.45 (2H, d, J=8.4 Hz, ArH), 7.08-7.44 (4H, br, ArH), 5.73 (2H, s, ArOCH₂O), 4.88 (2H, d, J=14.1 Hz, ArCH₂N), 3.68 (2H, d, J=14.1 Hz, ArNCH₂), 3.42-3.60 (2H, m, NCH₂), 2.92-3.09 (2H, m, NCH₂), 0.62 (6H, t, J=7.2 Hz, CH₃); $[\alpha]_D^{22}$ −8.4° (c 0.5, MeOH).

Example 1-6

Compound of Example 1-6 was synthesized in the same manner as Example 1-1.

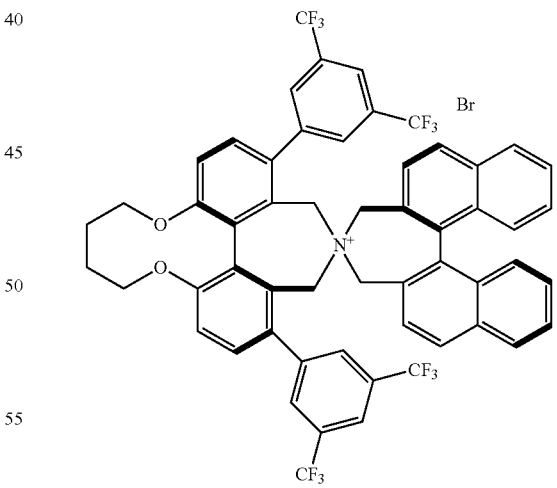

¹H NMR (300 MHz, CDCl₃) δ 8.19 (2H, s, ArH), 7.81 (2H, d, J=8.1 Hz, ArH), 7.68 (2H, d, J=9.0 Hz, ArH), 7.42-7.55 (4H, m, ArH), 7.15-7.33 (8H, m, ArH), 7.05 (2H, d, J=8.7 Hz, ArH), 6.07 (2H, d, J=8.7 Hz, ArH), 4.62 (2H, d, J=13.5 Hz, ArCH₂N), 4.59 (2H, d, J=13.5 Hz, ArCH₂N), 4.48 (2H, d, J=13.8 Hz, ArCH₂N), 4.36-4.56 (4H, m, ArOCH₂), 3.65 (2H, d, J=13.8 Hz, ArCH₂N), 1.57-2.11 (4H, m, CH₂); $[\alpha]_D^{29}$ +112.32° (c 0.43, CHCl₃).

Example 1-7

Compound of Example 1-7 was synthesized in the same manner as Example 1-1.

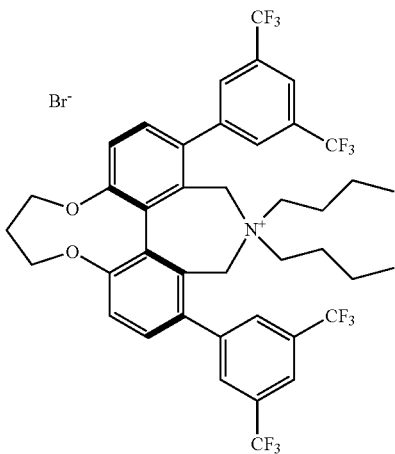

$^1$H NMR (300 MHz, acetone-d$_6$) δ 8.17-8.36 (6H, m, ArH), 7.70 (2H, d, J=8.4 Hz, ArH), 7.64 (2H, d, J=8.4 Hz, ArH), 4.73 (2H, d, J=14.1 Hz, ArCH$_2$N), 4.52-4.70 (2H, m, ArOCH$_2$), 3.97 (2H, d, J=14.1 Hz, ArCH$_2$N), 3.14-3.26 (2H, m, NCH$_2$), 2.10-2.25 (2H, m, NCH$_2$), 0.75-1.45 (8H, m, CH$_2$), 0.60 (6H, t, J=7.5 Hz, CH$_3$); $[\alpha]_D^{26}$ –37.0° (c 1.0, MeOH).

Example 2

Preparation of Optically Active α,α-Disubstituted Glycine Derivative

Example 2-1

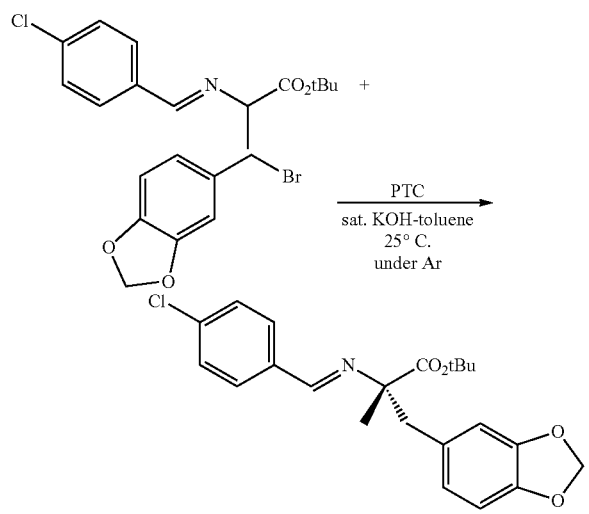

Alanine Schiff base (0.25 mmol) shown in the reaction formula, piperonyl bromide (0.3 mmol) and phase-transfer catalyst PTC (0.02 mol %) were dissolved in a toluene solvent (2 mL) The mixed solution was stirred vigorously, and a saturated aqueous KOH solution (0.5 mL) was added dropwise thereto. Under an argon atmosphere, the mixture was stirred vigorously at 25° C. (constant-temperature bath) until the reaction was completed. After the reaction was completed, 0.25 mmol methyl benzoate was added as the internal standard material, and the reaction mixture was served as it is for $^1$HNMR analysis to determine the yield (quantitative).

The reaction mixture was extracted, concentrated, and dried, and then purified by column chromatography. Then, the substance of interest was obtained as an amine derivative wherein the imine moiety was deprotected. This amine derivative was dissolved in a methylene chloride solution, and benzoyl chloride (0.25 mmol) was added dropwise thereto. After 1 hour, the reaction was quenched by an ammonia water, followed by extraction and column purification (hexane:ethyl acetate=7:1) to obtain a benzoylated derivative. The optical purity was determined by an HPLC analysis of the benzoylated derivative (Chiral Cell AD-H, hexane:isopropanol:ethanol=90:5:5) (95% ee).

Note) Phase-transfer catalyst PTC: the optically active 6,7-dihydro-5H-dibenzo[c,e]azepine derivative synthesized in Example 1-1

Example 2-2

The same alanine Schiff base (0.25 mmol) as used in Example 2-1, benzyl bromide (0.3 mmol) and the same phase-transfer catalyst PTC as used in Example 2-1 (0.02 mol %) were dissolved in a toluene solvent (2 mL). The mixed solution was stirred vigorously, and a saturated aqueous KOH solution (0.5 mL) was added dropwise thereto. Under an argon atmosphere, the mixture was stirred vigorously at 25° C. (constant-temperature bath) until the reaction was completed. After the reaction was completed, 1N hydrochloric acid was added to the organic phase and the mixture was stirred at room temperature for 3 hours. After the reaction was completed, the aqueous phase was collected and sodium carbonate was added to alkalify the solution, which was then extracted with ethyl acetate to obtain a deprotected amine derivative. This amine derivative was dissolved in a methylene chloride solution, and benzoyl chloride (0.25 mmol) was added dropwise thereto. After 1 hour, the reaction was quenched by an ammonia water, followed by extraction and column purification (hexane:ethyl acetate=7:1) to obtain a benzoylated derivative. The optical purity was determined by an HPLC analysis of the benzoylated derivative (Chiral Cell AD-H, hexane:isopropanol:ethanol=90:5:5) (97% ee).

INDUSTRIAL APPLICABILITY

By using the compound of the present invention as a catalyst, an optically active disubstituted glycine derivative with high optical purity can be obtained easily and efficiently.

The invention claimed is:

1. An optically active 6,7-dihydro-5H-dibenzo[c,e]azepine derivative represented by formula (1):

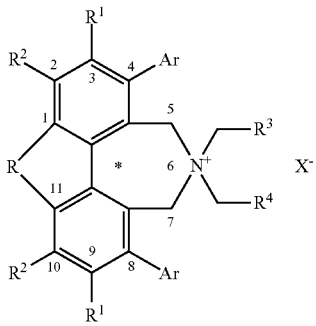 (1)

where:
R is represented by formula (2):

—O—R'—O—  (2)

wherein R' represents —(CH$_2$)$_n$— that may have a substituent selected from the group consisting of:
  a halogen atom,
  a linear, branched, or cyclic C1-C8 alkyl group,
  a linear, branched, or cyclic C1-C8 alkoxy group,
  an oxo group,
  an aryl group,
  an arylcarbonyl group,
  an alkylcarbonyl group,
  an arylsulfonyl group, and
  an alkylsulfonyl group;
n is an integer of 1 to 8;
R$^1$ and R$^2$ are the same or different, and represent:
  a hydrogen atom;
  a halogen atom;
  a linear, branched, or cyclic C1-C8 alkyl group that may have a substituent selected from the group consisting of:
    a halogen atom,
    a C6-C14 aryl group, and
    a linear, branched, or cyclic C1-C8 alkoxy group; or
  a C6-C14 aryl group that may have a substituent selected from the group consisting of:
    a halogen atom,
    a linear, branched, or cyclic C1-C8 alkyl group, and
    a linear, branched, or cyclic C1-C8 alkoxy group;
R$^3$ and R$^4$ are the same or different, and represent a linear, branched, or cyclic C1-C30 alkyl group, or
R$^3$ and R$^4$ together form

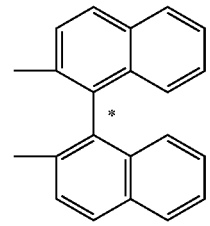 [SMILES: Cc1ccc2ccccc2c1-c1c(C)ccc2ccccc12]

wherein * represents optical activity;
  Ar represents a C6-C14 aryl group that may have a substituent selected from the group consisting of:
    a halogen atom,
    a linear, branched, or cyclic C1-C8 alkyl group,
    a linear, branched, or cyclic C1-C8 alkoxy group,
    a linear, branched, or cyclic C1-C8 alkylcarbonyl group,
    a linear, branched, or cyclic C1-C8 alkylsulfonyl group,
    a C6-C14 arylcarbonyl group, and
    a C6-C14 arylsulfonyl group; or
  Ar represents a C3-C8 heteroaryl group that may have a substituent selected from the group consisting of:
    a halogen atom,
    a linear, branched, or cyclic C1-C8 alkyl group,
    a linear, branched, or cyclic C1-C8 alkoxy group,
    a linear, branched, or cyclic C1-C8 alkylcarbonyl group,
    a linear, branched, or cyclic C1-C8 alkylsulfonyl group,
    a C6-C14 arylcarbonyl group, and
    a C6-C14 arylsulfonyl group;
X— represents a counter anion; and
* represents optical activity.

* * * * *